(12) United States Patent
Krauter et al.

(10) Patent No.: US 7,819,798 B2
(45) Date of Patent: Oct. 26, 2010

(54) INSERTION TUBE STORAGE CAROUSEL

(75) Inventors: Allan I. Krauter, Skaneateles, NY (US); Charles W. Fish, III, Tully, NY (US); Raymond A. Lia, Auburn, NY (US); Thomas W. Karpen, Skaneateles, NY (US); Kenneth Von Felten, Freeville, NY (US); Ronald H. Lawson, Seneca Falls, NY (US); Leigh Lawson, legal representative, Seneca Falls, NY (US)

(73) Assignee: GE Inspection Technologies, LP, Skaneateles, NY (US)

( * ) Notice: Subject to any disclaimer, the term of this patent is extended or adjusted under 35 U.S.C. 154(b) by 1160 days.

(21) Appl. No.: 11/474,142

(22) Filed: Jun. 23, 2006

(65) Prior Publication Data

US 2007/0156018 A1 Jul. 5, 2007

Related U.S. Application Data

(60) Provisional application No. 60/693,824, filed on Jun. 24, 2005.

(51) Int. Cl.
*A61B 1/00* (2006.01)

(52) U.S. Cl. .............. 600/102; 600/101; 206/570; 206/363; 248/75; 248/78

(58) Field of Classification Search .......... 600/102, 600/101; 206/570, 702, 389, 363, 408, 409; 248/75, 78, 89, 312, 146; 242/588, 588.3, 242/588.6, 360, 361.1, 361.2, 361.4, 613.1, 242/311.2, 597.8, 613; 220/631, 635, 628, 220/623, 610, 601, 604, 620
See application file for complete search history.

(56) References Cited

U.S. PATENT DOCUMENTS

| 355,924 A | 1/1887 | Favel |
|---|---|---|
| 752,889 A | 2/1904 | Dieckmann |

(Continued)

FOREIGN PATENT DOCUMENTS

AU 775955 7/2001

(Continued)

OTHER PUBLICATIONS

Olympus News Release, Olympus PT36-300 Pipe Inspection System, http://www.olympus.co.jp/en/news/1998b/nr/980929pt36e.cfm?chm-4, Sep. 29, 1998, 3 pgs.
Envirosight LLC., http://www.envirosight.com/home.html, 2003, 1 pg.
Rigid Seesnake Plus, http://www.rigid.com/seeit/, 2004, 1 pg.
Pearpoint, http//www.pearpoint.com/large_pushrod.htm, 2004, 1 pg.
Everest VIT, Inc., Everest VIT Completely Focused on Products, http://222.inspektionssystem.se/datablad/everestvit/default.asp, 2002, 1 pg.

(Continued)

*Primary Examiner*—Matthew J Kasztejna
(74) *Attorney, Agent, or Firm*—Global Patent Operation; Mark A. Conklin

(57) ABSTRACT

An apparatus for storing at least one elongated and flexible object, such as an insertion tube that functions as a portion of an endoscope or a borescope device. The apparatus includes a rotating storage carousel having a base and a peripheral barrier. An elongated and flexible object, such as an insertion tube, is stored along the inner side of the peripheral barrier and the base. The storage cavity of the carousel rotates while accepting the transfer of the elongated and flexible object for storage.

7 Claims, 16 Drawing Sheets

U.S. PATENT DOCUMENTS

| | | | |
|---|---|---|---|
| 1,532,177 A * | 4/1925 | Gist | 248/89 |
| 1,942,388 A * | 1/1934 | Ash | 242/387 |
| 2,286,904 A * | 6/1942 | Ewald | 137/355.26 |
| 2,300,243 A * | 10/1942 | Zierden | 242/387 |
| 2,397,975 A | 4/1946 | Obermaier | |
| 2,924,495 A | 2/1960 | Haines | |
| 3,665,991 A | 5/1972 | Gillemot et al. | |
| 3,850,487 A | 11/1974 | Batchelor | |
| 3,957,159 A | 5/1976 | Radek | |
| 4,116,338 A | 9/1978 | Weichselbaum | |
| 4,170,234 A | 10/1979 | Graham | |
| 4,256,225 A | 3/1981 | Jackson | |
| 4,258,966 A | 3/1981 | Grubb, Jr. | |
| D260,617 S | 9/1981 | Lawson, II et al. | |
| 4,287,154 A | 9/1981 | Sommers | |
| 4,436,267 A | 3/1984 | Eads et al. | |
| 4,445,579 A | 5/1984 | Bello | |
| 4,557,430 A * | 12/1985 | Bonhard | 242/405.3 |
| 4,572,370 A | 2/1986 | Cedenblad et al. | |
| 4,579,230 A | 4/1986 | Reid, Jr. | |
| 4,607,746 A | 8/1986 | Stinnette | |
| 4,700,693 A | 10/1987 | Lia et al. | |
| 4,727,859 A | 3/1988 | Lia | |
| 4,733,937 A | 3/1988 | Lia et al. | |
| 4,735,501 A | 4/1988 | Ginsburgh et al. | |
| 4,787,369 A | 11/1988 | Allred, III et al. | |
| 4,790,294 A | 12/1988 | Allred, III et al. | |
| 4,794,912 A | 1/1989 | Lia | |
| 4,796,607 A | 1/1989 | Allred, III et al. | |
| 4,853,774 A | 8/1989 | Danna et al. | |
| 4,862,253 A | 8/1989 | English et al. | |
| 4,887,154 A | 12/1989 | Wawro et al. | |
| 4,909,600 A | 3/1990 | Ciarlei et al. | |
| 4,913,369 A | 4/1990 | Lia et al. | |
| 4,933,816 A | 6/1990 | Hug et al. | |
| 4,941,454 A | 7/1990 | Wood et al. | |
| 4,941,456 A | 7/1990 | Wood et al. | |
| 4,962,751 A | 10/1990 | Krauter | |
| 4,980,763 A | 12/1990 | Lia | |
| 4,989,581 A | 2/1991 | Tamburrino et al. | |
| 4,989,582 A * | 2/1991 | Sakiyama et al. | 600/109 |
| 4,998,182 A | 3/1991 | Krauter et al. | |
| 5,014,515 A | 5/1991 | Krauter | |
| 5,014,600 A | 5/1991 | Krauter et al. | |
| 5,018,436 A | 5/1991 | Evangelista et al. | |
| 5,018,506 A | 5/1991 | Danna et al. | |
| 5,019,121 A | 5/1991 | Krauter | |
| D318,627 S | 7/1991 | Frederick | |
| 5,047,848 A | 9/1991 | Krauter | |
| 5,052,803 A | 10/1991 | Krauter | |
| 5,061,995 A | 10/1991 | Lia et al. | |
| 5,066,122 A | 11/1991 | Krauter | |
| 5,070,401 A | 12/1991 | Salvati et al. | |
| 5,074,421 A | 12/1991 | Coulter | |
| 5,114,636 A | 5/1992 | Evangelista et al. | |
| 5,140,975 A | 8/1992 | Krauter | |
| 5,160,101 A | 11/1992 | Ferraro et al. | |
| 5,191,879 A | 3/1993 | Krauter | |
| 5,202,758 A | 4/1993 | Tamburrino | |
| 5,203,319 A | 4/1993 | Danna et al. | |
| 5,275,152 A | 1/1994 | Krauter et al. | |
| 5,278,642 A | 1/1994 | Danna et al. | |
| 5,314,070 A | 5/1994 | Ciarlei | |
| 5,323,899 A | 6/1994 | Strom et al. | |
| 5,345,339 A | 9/1994 | Knieriem et al. | |
| 5,347,989 A | 9/1994 | Monroe et al. | |
| 5,365,331 A | 11/1994 | Tamburrino et al. | |
| 5,373,317 A | 12/1994 | Salvati et al. | |
| D358,471 S | 5/1995 | Cope et al. | |
| 5,435,296 A | 7/1995 | Vivenzio et al. | |
| 5,633,675 A | 5/1997 | Danna et al. | |
| 5,641,080 A | 6/1997 | Humphrey et al. | |
| 5,701,155 A | 12/1997 | Wood et al. | |
| 5,734,418 A | 3/1998 | Danna | |
| 5,754,220 A | 5/1998 | Smalser, Sr. | |
| 5,754,313 A | 5/1998 | Pelchy et al. | |
| 5,806,822 A | 9/1998 | Schulz | |
| 5,857,963 A | 1/1999 | Pelchy et al. | |
| 5,924,977 A * | 7/1999 | Yabe et al. | 600/121 |
| 6,066,089 A | 5/2000 | Costello et al. | |
| 6,083,152 A | 7/2000 | Strong | |
| 6,097,848 A | 8/2000 | Salvati | |
| 6,109,460 A | 8/2000 | Herlevi et al. | |
| 6,310,647 B1 | 10/2001 | Parulski et al. | |
| 6,339,861 B1 | 1/2002 | Snyder | |
| 6,375,017 B1 | 4/2002 | Schattner et al. | |
| 6,468,201 B1 | 10/2002 | Burdick | |
| 6,483,535 B1 | 11/2002 | Tamburrino et al. | |
| 6,494,739 B1 | 12/2002 | Vivenzio et al. | |
| 6,499,608 B1 | 12/2002 | Sterling et al. | |
| 6,538,732 B1 | 3/2003 | Drost et al. | |
| 6,545,704 B1 | 4/2003 | Olsson et al. | |
| 6,590,470 B1 | 7/2003 | Burdick | |
| 6,677,983 B1 | 1/2004 | Takahashi et al. | |
| 6,807,982 B1 * | 10/2004 | Ames | 137/355.28 |
| 6,830,545 B2 | 12/2004 | Bendall | |
| 6,846,285 B2 | 1/2005 | Hasegawa et al. | |
| 6,953,432 B2 | 10/2005 | Schiefer | |
| 7,134,993 B2 | 11/2006 | Lia et al. | |
| 7,170,677 B1 | 1/2007 | Bendall et al. | |
| 2004/0019252 A1 | 1/2004 | Hirata | |
| 2004/0054254 A1* | 3/2004 | Miyake | 600/104 |
| 2004/0054259 A1 | 3/2004 | Hasegawa et al. | |
| 2004/0183900 A1 | 9/2004 | Karpen et al. | |
| 2004/0200032 A1 | 10/2004 | Morgan et al. | |
| 2004/0204628 A1 | 10/2004 | Rovegno | |
| 2004/0215413 A1 | 10/2004 | Weldum et al. | |
| 2004/0242958 A1 | 12/2004 | Fujikawa et al. | |
| 2005/0050707 A1 | 3/2005 | Scott et al. | |
| 2005/0054899 A1 | 3/2005 | Miyake | |
| 2005/0129108 A1 | 6/2005 | Bendall et al. | |
| 2005/0162643 A1 | 7/2005 | Karpen | |
| 2005/0165275 A1 | 7/2005 | Von Felten et al. | |
| 2005/0281520 A1 | 12/2005 | Kehoskie et al. | |
| 2006/0050983 A1 | 3/2006 | Bendall et al. | |
| 2006/0072903 A1 | 4/2006 | Weldum et al. | |

FOREIGN PATENT DOCUMENTS

| | | |
|---|---|---|
| CN | 1426752 | 7/2003 |
| CN | 1463672 | 12/2003 |
| FR | 2368860 | 5/1978 |
| GB | 0772636 | 4/1957 |
| JP | 1057299 | 3/1989 |
| JP | 2001154117 | 6/2001 |
| JP | 2004209144 | 7/2004 |
| JP | 2005323778 | 11/2005 |

OTHER PUBLICATIONS

Envirosight LLC., http://wwwenvirosight.com/products/envirocam.html, 2004, pgs.

Olympus Industrial, IPLEX and IPLEX SA Systems, http://222.olympusindustrial.com/index.cfm/page/products.index.cfm/cid/17/navid/197/p, 2004, 4 pgs.

International Search Report dated Nov. 17, 2006 and received in connection with foreign counterpart application PCT/US2006/024676.

* cited by examiner

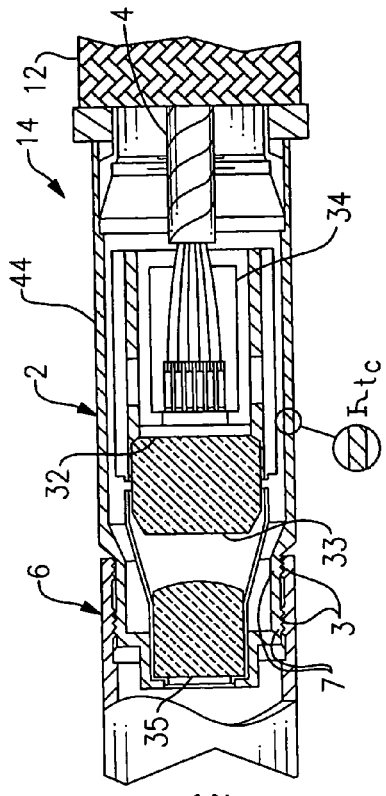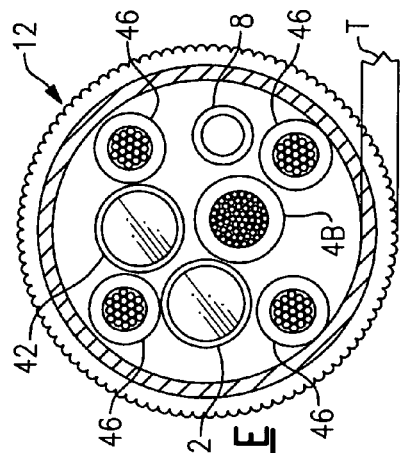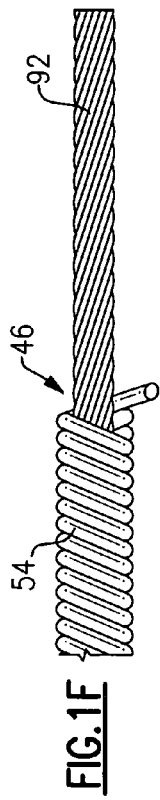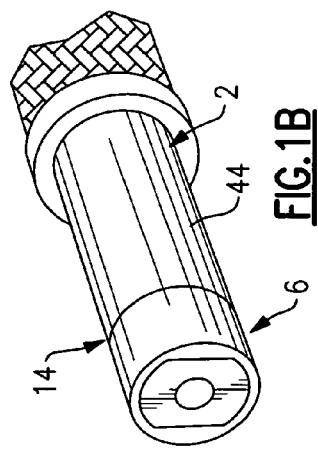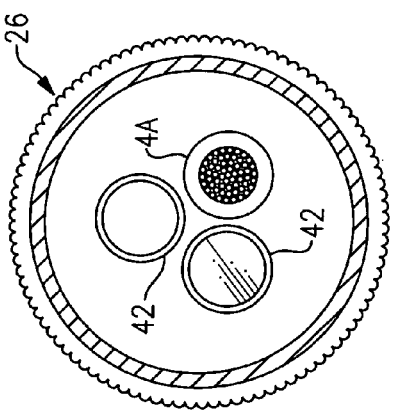
FIG.1C
FIG.1E
FIG.1F
FIG.1B
FIG.1D

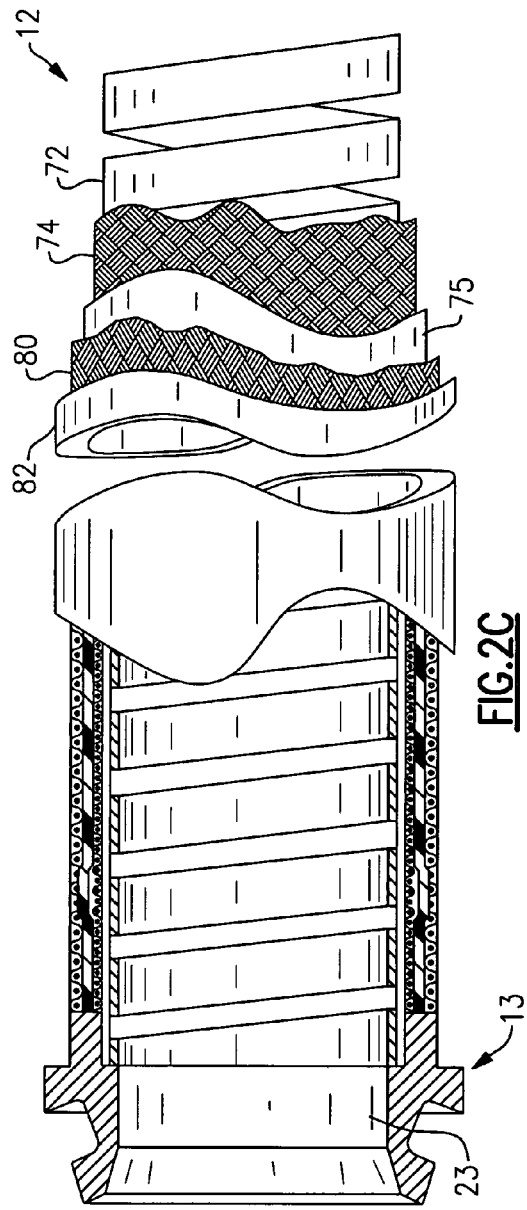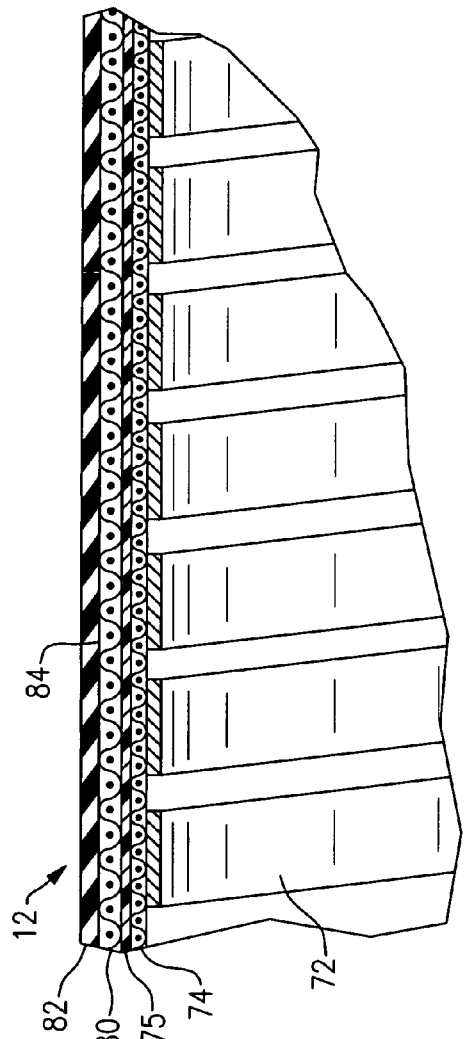
FIG.2C
FIG.2D

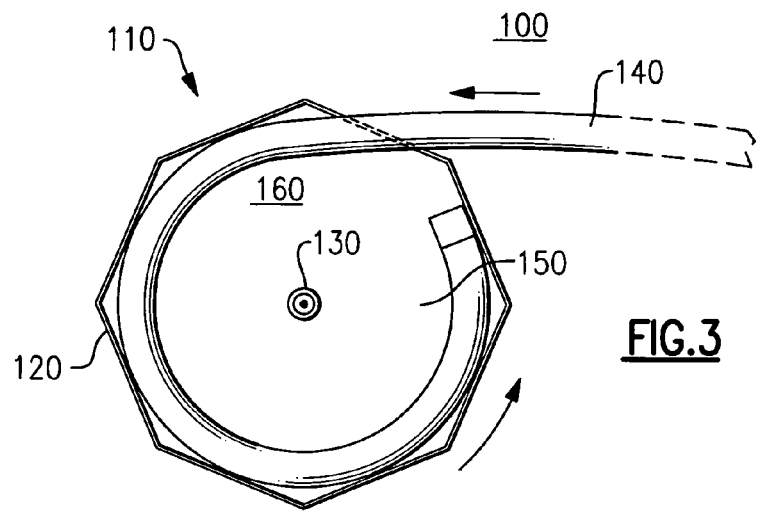
FIG. 3
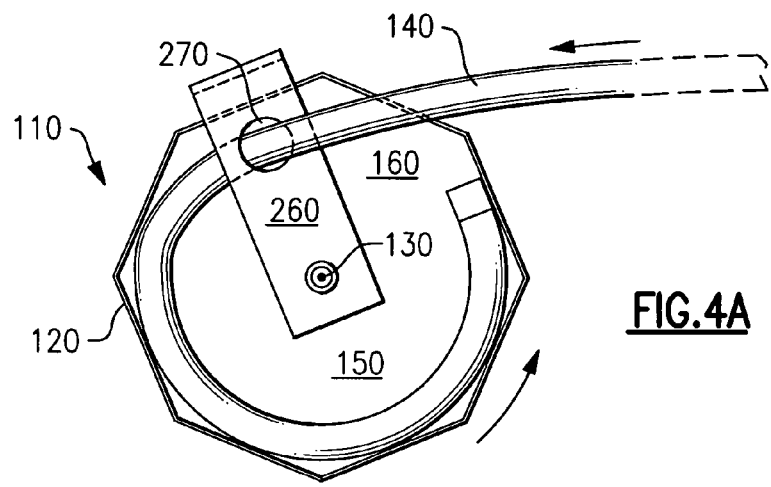
FIG. 4A
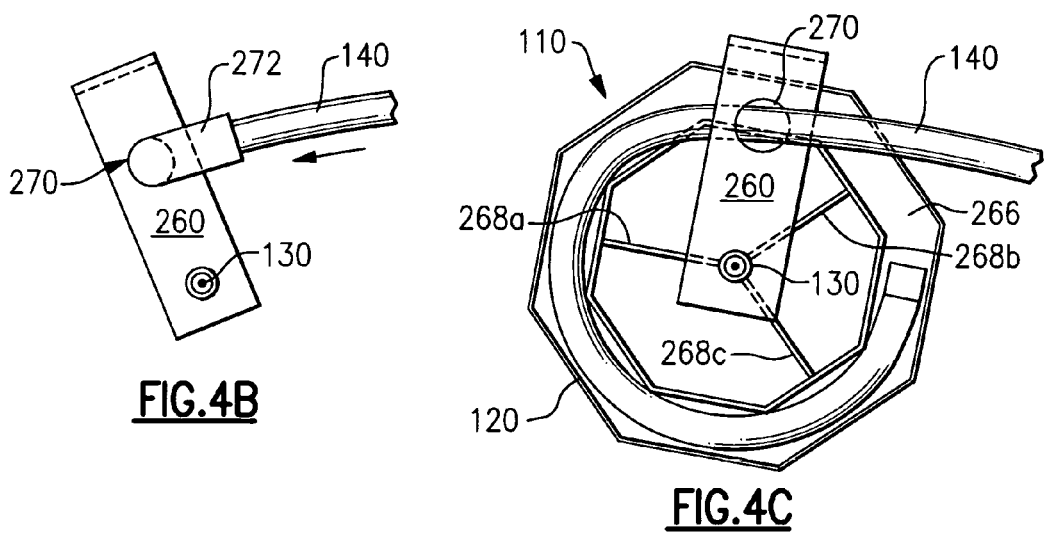
FIG. 4B
FIG. 4C

INSERTION TUBE STORAGE CAROUSEL

CROSS-REFERENCE TO RELATED APPLICATIONS

This non-provisional patent application claims priority to a provisional U.S. patent application having Ser. No. 60/693,824, that is titled "Insertion Tube Storage Carousel", that was filed Jun. 24, 2005 and that is incorporated herein by reference in its entirety.

CROSS-REFERENCE TO APPLICATIONS INCLUDING RELATED SUBJECT MATTER

This patent application includes subject matter that is related to that of U.S. patent application Ser. No. 10/768,761, that is titled "Remote Video Inspection System", that was filed Jan. 29, 2004 and that is incorporated herein by reference in its entirety.

FIELD OF THE INVENTION

This invention relates generally to an apparatus for storing at least one elongated and flexible object, and specifically to an apparatus for storing at least one insertion tube of the type that functions as a portion of an endoscope or a borescope device.

BACKGROUND OF THE INVENTION

An insertion tube remote viewing device, such as an endoscope or a borescope, is generally characterized as having an elongated and flexible insertion tube with a viewing head at its forward (distal) end, and a control section at its rear (proximal) end. An endoscope is generally used for remotely inspecting the interior portions of a body cavity for the purpose medical diagnosis or treatment. A borescope is generally used for inspection of interior portions of industrial equipment.

Image information is communicated through the insertion tube from the viewing head to the control section. The image information is displayed onto a video screen for viewing by an operator. Typically, an insertion tube is 10 to 100 feet in length and approximately ⅛" to ½" in diameter, though tubes of other lengths and diameters are possible, depending on the application.

The storage of insertion tubes can be problematic. One approach stores an insertion tube within a spiral-shaped storage cavity of a remote viewing device carrying case. The storage cavity is sized and shaped to accept the transfer of an insertion tube of a borescope. A user stores the insertion tube into the carrying case by first inserting and pushing its distal end into the opening of the spiral-shaped storage cavity. The user then pushes the remainder of the insertion tube into the opening of the spiral-shaped storage cavity until the entire insertion tube is transferred into the cavity.

The pushing force required is usually a function of the friction between the spiral-shaped storage cavity and the insertion tube. For long insertion tubes, the friction and the pushing force required to counteract the friction can become excessively high. Consequently, an entire insertion tube cannot be stored into the carrying case without substantial effort. Furthermore, the spiral-shaped storage cavity can cause the insertion tube to twist and/or torque during the storage procedure, creating the potential for damaging the insertion tube itself or harming the delicate optical components often located at the distal end of the insertion tube.

Other mechanisms for storing an elongated and flexible object include a rotating reel (drum) type of mechanism where a type of handle is attached to the reel. The reel can be structured from a wire frame or solid surface material and may surround a coiled wire, rod or tube. Manufacturers such as Olympus, Rigid, Envirosight, Pearpoint and EverestVIT have manufactured these types of reels. The handle and the reel are rotated in order to wrap an insertion tube or other type of elongated object around the reel. Other mechanisms turn a reel by means other than a handle. For example, a spring-loaded reel pulls an electrical power cord into a vacuum cleaner. With this type of approach, the electrical power cord is wound onto the outside of the spring-loaded reel, referred to as a take-up reel. This type of mechanism is not well-suited to store objects, such as a borescope insertion tube, that resist coiling due to the objects' bending stiffness.

SUMMARY OF THE INVENTION

In one aspect, the invention provides an apparatus for storing an insertion tube of a remote viewing device, such as of a borescope and/or an endoscope device. The apparatus includes a storage carousel including a rotatable cavity bounded by at least one inner surface, that includes an inner surface of a base and an inner surface of a peripheral barrier, and where the rotatable cavity is configured to rotate around an axis of rotation and configured to accommodate the storage of an insertion tube having a proximal end and distal end.

In some embodiments, the apparatus also includes a frame providing mechanical support to a pivot shaft and includes an insertion port having an angle of orientation and configured to guide a transfer of said insertion tube to or from the rotatable cavity; and where the at least one inner surface is configured to make physical contact and to generate a frictional force between the insertion tube and the at least one inner surface so that the transfer of said insertion tube to or from the rotatable cavity causes the rotatable cavity to rotate.

In some embodiments, the rotatable cavity is of a conical shape and has a larger diameter located more proximate to the base and a smaller diameter located less proximate to the base. In some embodiments, the rotatable cavity of a conical shape forms an acute angle adjacent to an intersection of the inner surface of the peripheral barrier and the inner surface of the base, and the acute angle is configured to receive an insertion tube and to enhance the frictional contact with the insertion tube.

Optionally, the inner surface of the storage carousel is constructed from materials designed to further enhance the frictional contact between the insertion tube and the storage carousel. The at least one inner surface is configured to make physical contact with the insertion tube having both a proximal end and a distal end. In some embodiments, the apparatus includes a motor and the rotatable cavity of the storage carousel rotates in response to a force generated by the motor.

Optionally, the base is an angled base and the angled base is configured to form an acute angle adjacent to an intersection of the inner surface of the peripheral barrier and the inner surface of the base, and where the acute angle is configured to receive and to make physical contact with the insertion tube and to enhance the frictional contact between the at least one inner surface and the insertion tube.

In some embodiments, the storage carousel is located within a case storing components of a borescope or endoscope device. In other embodiments, the storage carousel is attached to an outer surface of a case storing components of a borescope or endoscope device. In yet other embodiments, the storage carousel is located separate from a case storing components of a borescope or endoscope device.

Optionally, the apparatus includes an outer casing enclosing the storage carousel and includes a cover plate, the cover plate includes an insertion port configured to guide the transfer of the insertion tube to or from the rotatable cavity and in a direction either towards or away the proximal end of the insertion tube.

Optionally, apparatus includes an insertion port having an angle of orientation and is configured to guide the transfer of the insertion tube to or from the rotatable cavity and in a direction either towards or away from the proximal end of the insertion tube. The apparatus can also include a frame that provides mechanical support to the storage of the carousel, and where the frame includes an insertion port.

In some embodiments, the apparatus includes a pivot shaft and a frame, the pivot shaft having a first and a second end and a longitudinal axis that is disposed co-linear with the axis of rotation, and where the first end of the pivot shaft is attached to the base and the second end of the pivot shaft is rotatably attached to the frame.

In another aspect, the invention is a video borescope system for remote visual applications including a handset that is configured for inputting commands from a user and a display that is configured for communicating information to the user, an insertion tube including a distal end and a proximal end that is attachable to the handset, the insertion tube is configured to illuminate and to capture an image from an area surrounding the distal end, a storage carousel including a rotatable cavity adjacent to an insertion port, the rotatable cavity being enclosed by a peripheral barrier and a base that collectively have at least one inner surface, the at least one inner surface is configured to cause frictional contact with the insertion tube when the insertion tube is transferred to or from the rotatable cavity via the insertion port, the contact generates a frictional force upon the at least one inner surface so that when the insertion tube is transferred to or from the rotatable cavity, the rotatable cavity will rotate around an axis in a direction in which the insertion tube is being transferred.

In another aspect, the invention is an apparatus for storing an elongated flexible object, including a storage carousel having a base, a peripheral barrier, and an axis of rotation, the base substantially defining at least one inner surface that intersects the axis of rotation, the peripheral barrier having an inner surface that surrounds the axis of rotation, a rotatable cavity that is bounded by the inner surface of the base and the inner surface of the peripheral barrier; and where the storage carousel is configured to rotate around the axis of rotation and the rotatable cavity is configured to accommodate the storage of an elongated flexible object disposed along the inner surface of the peripheral barrier and/or of the inner surface of the base, the elongated flexible object having both a proximal end and a distal end, and where the storage carousel includes a conical shaped peripheral barrier, the conical shaped peripheral barrier provides a rotatable cavity with a larger diameter located proximate to the base and a smaller diameter located farther away from the base. Optionally, the elongated flexible object is an insertion tube for a remote viewing device, such as for a borescope or an endoscope device.

In another aspect, the invention is a method of storing an insertion tube of an endoscope inside a storage device including the steps of providing a rotatable cavity that is rotatable around an axis of rotation and that is bounded by at least one inner surface, transferring a distal end of an insertion tube into the cavity through an insertion port, causing the cavity to rotate via a friction force resulting from physical contact between a portion of the insertion tube and the at least one an inner surface, transferring the insertion tube further into the cavity to cause further rotation of the cavity and to cause storage of a substantial portion of the insertion tube within the cavity so that a proximal end of the insertion tube is located proximal to the insertion port.

In some embodiments, the at least one inner surface includes an inner surface of a base and the rotatable cavity is of a conical shape has a larger diameter located more proximate to the base and a smaller diameter located less proximate to the base.

In some embodiments, the at least one inner surface includes an inner surface of a base and an inner surface of a peripheral barrier, and the base is an angled base and an acute angle is defined adjacent to an intersection of the inner surface of the base and the inner surface of the peripheral barrier, and the acute angle is configured to receive and to make physical contact with the insertion tube and to enhance the frictional contact between the at least one inner surface and the insertion tube.

BRIEF DESCRIPTION OF THE DRAWINGS

The objects and features of the invention can be better understood with reference to the following invention description, claims and drawings. The following descriptions of various embodiments of the invention are exemplary and not intended to be limiting, unless otherwise specifically described. The drawings are not necessarily to scale and the emphasis is instead generally being placed upon illustrating the principles of the invention. Within the drawings, like reference numbers are used to indicate like parts throughout the various views. Differences between like parts may cause those parts to be indicated by different reference numbers. Unlike parts are indicated by different reference numbers.

FIGS. 1A-1F illustrate various aspects and components of a first embodiment of an insertion tube remote viewing device having an insertion tube that can be stored in accordance with the invention.

FIGS. 2A-2G illustrate a second embodiment of an insertion tube remote viewing device and various aspects of an embodiment of an insertion tube that can be stored in accordance with the invention.

FIG. 3 illustrates a top view of an insertion tube being transferred into a rotating storage carousel according to the present invention that includes a base, a peripheral barrier, and a pivot shaft that bounds a cavity for storing an elongated flexible object.

FIG. 4A illustrates a top view of the illustration of FIG. 3 further including a frame and an insertion port.

FIG. 4B illustrates an alternate embodiment of the invention of FIG. 4A further including an angled inlet tube.

FIG. 4C illustrates an alternate embodiment of the invention of FIG. 4A further including a partial base plate.

DETAILED DESCRIPTION OF THE INVENTION

Figure 1A:
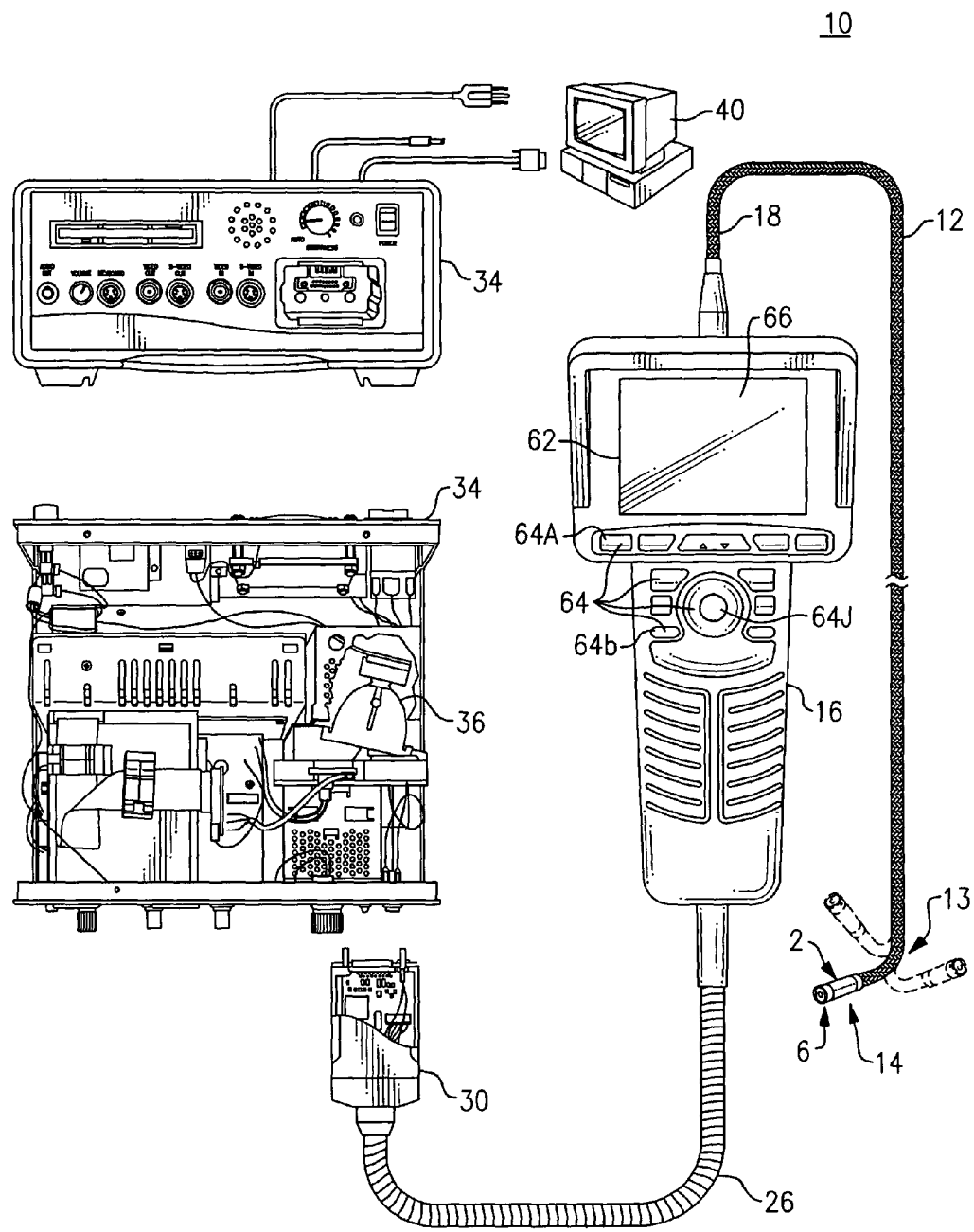

FIG. 1A illustrates a first embodiment of an remote viewing device 10, such as an endoscope or a borescope, including an insertion tube 12 that can be stored in accordance with the invention. As shown, the remote viewing device 10 includes a first embodiment of a base module 34, also referred to herein as a light box 34, a power plug 30, an umbilical cord 26, a handset 16, also referred to herein as a hand piece 16, an insertion tube 12 and a viewing head assembly 14.

Disposed within the light box 34 is a light source 36 such as a 50-Watt metal halide arc lamp. The light source 36 of light box 34 can direct light through the umbilical cord 26, through the handset 16, through the insertion tube 12 and outwardly through the viewing head assembly 14 to the environment surrounding a distal end 13 of the insertion tube 12. Alternatively, a light source can be located within other parts of the remote viewing device 10. For example, a light source can be located within the handset 16 or within the viewing head assembly 14.

In this embodiment, the umbilical cord 26 and the insertion tube 12 each enclose a fiber optic illumination bundle including one or more optical fibers. Light is generated and directed from the light source 36 through the optical fibers. Other embodiments of insertion tubes, implemented from various designs, can be used within the remote viewing device 10.

As shown, the viewing head assembly 14 includes a viewing head 2 and a detachable optical tip 6 that is configured to be readily detachable by a user. Alternatively, the optical tip 6 may be configured to be permanently attached to the viewing head 2. The viewing head assembly 14 also includes a canister 44 (FIGS. 1B and 1C) that surrounds an image sensor 32 (FIG. 1C) and a lens 33 (FIG. 1C). The canister 44 directs and focuses incoming light towards the image sensor 32. Other embodiments of viewing head assemblies, implemented from various designs, can be used within the remote viewing device 10.

The detachable optical tip 6 includes transparent material, such as a glass or plastic, that is configured to allow passage of light from the light source 36 to the environment surrounding the distal end 13 of the insertion tube 12. As shown, the viewing head 2 also includes a lens 35 for receiving incoming light from the surrounding environment. In other embodiments, the lens 35 is included within the optical tip 6. In other embodiments, the detachable optical tip 6 includes one or more light sources, such as one or more light emitting diodes (LED) that project light to the surrounding environment.

In this embodiment, the detachable optical tip 6 can be replaced by other embodiments of detachable optical tips having different operational characteristics, such as having different illumination characteristics and/or different light re-direction and/or light focusing and/or field/depth of view characteristics.

In some embodiments, an image processing circuit (not shown), residing within the light box 34, processes image information received by and communicated from the viewing head 2 to the light box 34. The image processing circuit can correct non-uniformities in a captured frame of image data that are attributable to non-uniformities of a light illumination pattern projected by the optical tip 6 of the device 10.

A handset display 62 and/or a monitor display 40 are configured to display a continuous video image. The handset 16 is configured to receive user command input via handset controls 64 in order to perform various operations of the remote viewing device 10. As shown, the handset 16 also includes a visual user interface 66 which is communicated to a user via the display 62.

A handset control circuit (not shown) inputs commands communicated by a user via the handset controls 64. The commands can direct movement of the distal end 13 of insertion tube 12 into an orientation desired by the user. The handset controls 64 include various control buttons 64A, 64B and a joystick 64J and provide a means for the user to communicate graphical user interface (GUI) commands to the remote viewing device 10.

In some embodiments, the image processing circuit and handset control circuits are microprocessor based and utilize one or a plurality of readily available programmable off-the-shelf microprocessor integrated circuit (IC) chips. Microprocessor IC chips have on-board volatile memory and nonvolatile memory that store and execute programming logic and are optionally in communication with external volatile and non-volatile memory devices.

The interior of the base module (light box) 34 is substantially occupied by various electrical components that are configured to support the operation of the remote viewing device 10. In addition to housing the image processing circuit, the base module (light box) 34 and power plug 30 also carry various electrical circuitries for delivering electrical power to various components of the remote viewing device 10.

FIG. 1B illustrates an embodiment of a viewing head assembly 14 disposed at the distal end 13 of the insertion tube 12 shown in FIG. 1. The viewing head assembly 14 includes the detachable optical tip 6 and a viewing head 2 that are attached to each other. The viewing head 2 includes a canister 44 that encapsulates the lenses 33, 35 and an image sensor 32 (shown in FIG. 1C) and elements of an image signal conditioning circuit (not shown).

FIG. 1C illustrates a cross-sectional view of the embodiment of the viewing head assembly 14 shown in FIGS. 1A-1B. As shown, the optical tip 6 includes threads 3 located along an interior surface of the optical tip 6. The threads 3 and the interior surface of the optical tip 6 surround and make physical contact with threads 7 located along an exterior surface of the canister 44 of the viewing head 2. As shown, the threads 3 are physically engaged with the threads 7 in order to attach the optical tip 6 to the viewing head 2. The lens 35 is disposed and aligned in series with the lens 33 of the viewing head 2.

As shown, the metal canister 44 encapsulates the lens 33, an image sensor 32 and an imager component circuit 34. The imager component circuit 34 includes an image signal conditioning circuit (not shown) and is also attached to a wiring cable bundle 4B (See FIG. 1E) that extends through the insertion tube 12 and that connects the viewing head 2 to the handset 16 (FIG. 1A). In the embodiment shown, a wiring cable bundle 4A (See FIG. 1D) is in communication with the wiring cable bundle 4B and extends through the umbilical cord 26 from the handset 16 to the power plug 30.

In other embodiments, other fasteners providing detachable attachment of the optical tip 6 to the viewing head 2 may be employed. Other embodiments of viewing heads implemented from various designs can be used to support the operation of the remote viewing device.

FIG. 1D illustrates a cross-sectional view of the umbilical cord 26 shown in FIG. 1A. The umbilical cord 26 encases a pair of fiber optic bundles 42. The umbilical cord 26 further encases the wiring cable bundle 4A that includes a first set (plurality) of wires. The first set of wires of the wiring cable bundle 4A extends from the power plug 30 to the handset 16 and communicates with a second set of wires that extend through the insertion tube 12. Other embodiments of umbilical cords that are implemented various designs can be used to support the operation of the remote viewing device.

FIG. 1E illustrates a cross-sectional view of the insertion tube 12 shown in FIG. 1A. The insertion tube 12 encases light conducting fiber optic bundles 42, a second wiring cable bundle 4B, (4) articulation cable assemblies 46, and a working channel 8. The second wiring cable bundle 4B includes the second set of wires that communicates with the first set of wires of the first wiring cable bundle 4A. The second set of wires of the second cable bundle 4B extends through the umbilical cord from the handset 16 to the viewing head 2.

The articulation cable assemblies 46 (FIG. 1E) are configured to enable the user (operator) to control bending of the insertion tube 12 at its distal end 13. The working channel 108 enables the user (operator) to manipulate a tool (e.g., a hook, a brush, or a magnet) extending from the distal end 13 of the insertion tube 12. Other embodiments of insertion tubes that are implemented from various designs can also be used to support the operation of the remote viewing device 10.

FIG. 1F illustrates one of the (4) articulation cable assemblies 46 that is disposed within the insertion tube 12 of FIG. 1E. The articulation cable assembly 46 includes a stranded cable 92 encased by an outer spring conduit 54. A tension force applied to one or more of the stranded cables 92 can cause the distal end 13 of the insertion tube to bend.

Figure 2A:
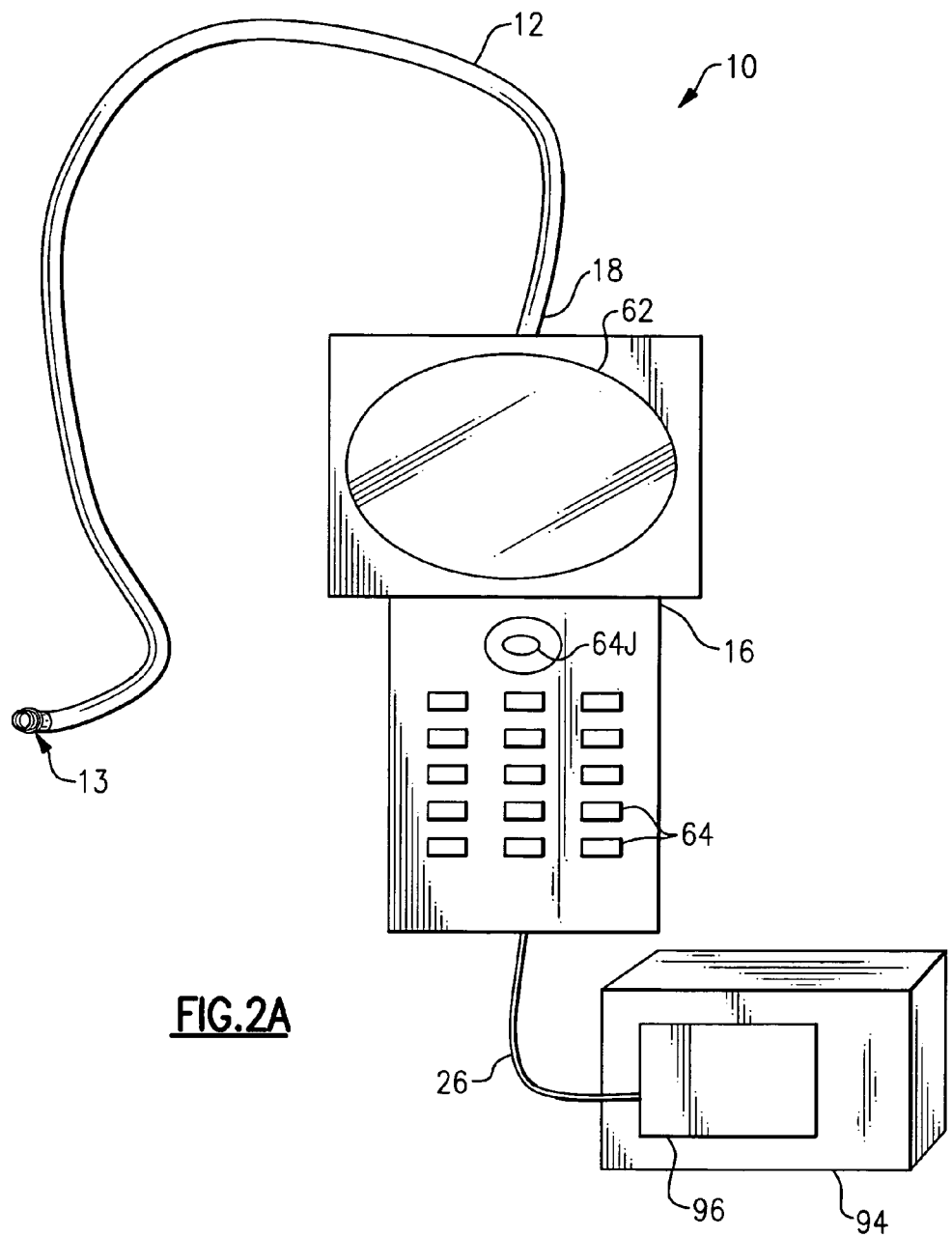

FIG. 2A illustrates an embodiment of a remote viewing device 10 like that shown in FIG. 1A. As shown, this embodiment includes a portable shipping/operating case 94 that includes a power supply 96 and a light source, such as a metal halide arc lamp (not shown). The shipping/operating case 94 is shown in operative communication with a handset 16 by means of an umbilical cord 26. The handset 16 can include, by way of example, an LCD monitor 62 (that can display images received by an imager), a joystick 64J to control articulation of a distal end 13 of an insertion tube 12, and a button set 64 to control the operation of the remote viewing device 10.

The handset 16 is connected to the insertion tube 12 that terminates at a distal end 13. The insertion tube 12 can be sized according to the desired application, by varying a diameter and a length of the insertion tube 12.

Figure 2B:
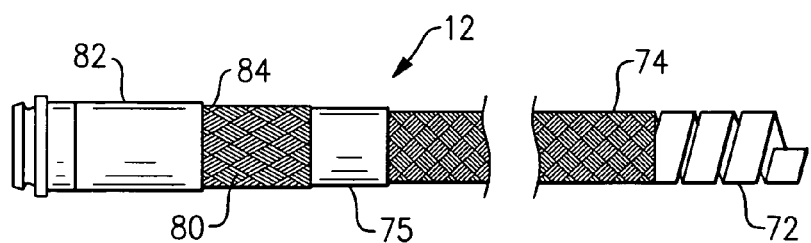

FIGS. 2B-2D illustrate the structure of an embodiment of an insertion tube 12 made in accordance with the invention. As shown, the insertion tube 12 includes a flexible helical coil 72, also referred to herein as a monocoil. The flexible helical coil 72 is a resilient structure that is configured for elastic deformation into a continuous curved shape. The flexible helical coil 72 can be, for example, a flexible spiral tube made from a thin section of stainless steel that is helically wound into a cylindrical tubular cross section. According to the present embodiment, the flexible helical coil 72 is made from stainless steel, although other structural materials may be substituted, such as, for example with aluminum, titanium and/or plastics.

A first braided tube 74, which in one embodiment is a net-like braided structure, formed of interwoven metallic or other fibers, is placed in an overlaying relation onto the entirety of the length of the flexible helical coil 72. The first braided tube 74 in the illustrative embodiment is configured to provide longitudinal stiffness for the insertion tube. In one embodiment, the first braided tube 74 is formed from groups of wires, in which each group of wires includes four wires. Each group of wires forms an angle with the longitudinal axis 98 of the first braided tube 74, this angle being referred to herein as the braid angle, which may be better understood by referring to FIGS. 2E and 2F.

Conventionally, the braid angle is kept constant along the entire length of the first braided tube and is approximately and typically 45 degrees, however, the braid angle of the first braided tube 74 of the present invention may be constant or may vary along the length of the first braided tube 74. As will be appreciated by those skilled in the art, for a given wire diameter and material used to make a braided tube, the closer the braid angle to the longitudinal axis 98 of the braided tube the stiffer the braided tube will be with respect to longitudinal extension and bending. Conversely, the further the braid angle is away from the longitudinal axis 98 of the braided tube, the more flexible the braided tube will be. Preferably, the braid angle at any point along the length of the first braided tube 74 is less than 45 degrees. In one embodiment of the present invention, the braid angle of the first braided tube 74 is maintained at approximately 45 degrees for the entire length of the first braided tube 74.

In an alternative embodiment, the braid angle of the first braided tube 74 varies along its length from approximately 15 degrees at the proximal end 18 (FIG. 2A) to approximately 45 degrees at the distal end 13. Varying the braid angle along the length of the first braided tube 74 in such a manner provides a more flexible region near the distal end of the insertion tube 12 and a stiffer region near the proximal end of the insertion tube 12. A more flexible distal end 13 makes it easier to bend the distal end 13 and its associated optics around obstacles, such as, for example, navigating sharp corners in a conduit. A stiffer proximal end makes it easier to push the insertion tube to overcome frictional forces ("sticking") and thereby advance the distal end and its associated optics deeper into the inspection area. In yet another embodiment, the braid angle of the first braided tube 74 is about 30 degrees for the entire length of the first braided tube 74.

The insertion tube 12 in the illustrative embodiment further includes an intermediate polymeric layer 75 over the first braided tube 74. The intermediate polymeric layer impregnates the first braided tube 74 but does not penetrate to the flexible helical coil 72. The intermediate polymeric layer 75 may be, for example, a layer of black polyurethane 0.010 inch thick having a Shore 80 A durometer reading. The intermediate polymeric layer may be applied by extrusion, spraying, brushing or other conventional polymer application techniques. Alternatively, the intermediate polymeric layer may be a preformed sleeve or sheath that is slideably engageable with the first braided tube 74 or the first braided tube 74 may be wrapped with a polymer covering.

A second braided tube 80, which preferably is a net-like braided structure, formed of interwoven metallic or other fibers, is placed in an overlaying relation onto the entirety of the length of the first braided tube 74 such that the intermediate polymeric layer is disposed between the first braided tube 74 and the second braided tube 80. The braid angle of the second braided tube 80 is selected to complement the braid angle of the first braided tube 74, thereby providing a desired amount of stiffness as well as promoting the even flexing of the insertion tube 12. The braid angle of the second braided tube 80 is used to promote the even flexing of the insertion tube 12 while the braid angle of the first braided tube 74 is used to control the bending and longitudinal stiffness of the insertion tube 12.

As will be appreciated by those skilled in the art, however, the functionality of the first and seconded braided tubes 74, 80 may be reversed such that the first braided tube 74 is configured to promote even flexing and the second braided tube 80 is configured to control the stiffness of the insertion tube 12. The braid angle of the second braided tube 80 may be either constant or vary along the length of the second braided tube 80.

In one embodiment, the second braided tube 80 has a constant braid angle of approximately 45 degrees. The second braided tube 80 is preferably made from tungsten wire or other suitable material. In one embodiment, the second braided tube 80 is constructed from 46 groups of NS-20 tungsten wire. Each of the 46 groups of NS-20 tungsten wire includes three wires. The second braided tube 80 is coupled to the distal and proximal ends 13, 18 of the flexible helical coil 72.

As shown, a thin polymeric layer 82 is applied to the outer peripheral surface of the second braided tube 80 and to the exterior portion of each end collar through conventional means such as, for example, spraying, painting, brushing, applying a preformed sleeve or sheath, or by wrapping. According to one embodiment, the polymer used is a two-part, low viscosity polyurethane dispersion which can be applied at room temperature and allowed to cure. Curing may take place at either room temperature or by placing the tubular assembly into an appropriately sized oven and heating, depending on the bonding requirements of the polymeric material used. Other suitable materials may also be used.

An end collar 23 (FIG. 2C) is attached to each of the distal and proximal ends 13, 18. According to one embodiment, each of the end collars 23 are cylindrical stainless steel members having an appropriately sized interior cavity, including an annular shoulder against which the ends of the tube sub-assembly are retained by soldering or adhesive bonding. The end collars 23 are attached after the tube sub-assembly has been cut to a pre-determined length. An end collar 23 that is attached to the distal end 13 is configured for engagement with an optical imaging and bending portion of (not shown) of the insertion tube 12 while the end collar 23 that is attached to the proximal end 18 is configured for engagement with a handset 16.

Figure 2E:
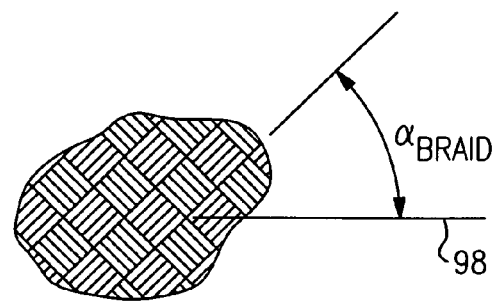
Figure 2F:
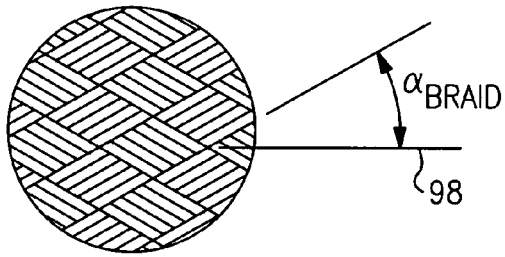

FIG. 2E shows a section of a braided tube having a braid angle $\alpha_{BRAID}$ of approximately 45 degrees. FIG. 2F shows a section of a braided tube having a braid angle $\alpha_{BRAID}$ of approximately 30 degrees. The first braided tube 74 may be made from a stainless steel or other suitable material, such as aluminum, titanium or alloys thereof, or plastics and polymers. In one embodiment, the first braided tube 74 is configured to be an electro-magnetic interference inhibiting shield, such as, for example, by constructing it 74 from stainless steel wire or other electro-magnetic interference inhibiting material. According to the present embodiment, the first braided tube 74 is soldered or otherwise fixedly attached to the flexible helical coil 72 (See FIG. 2B), at respective distal and proximal ends 13, 18 (See FIG. 1A).

Figure 2G:
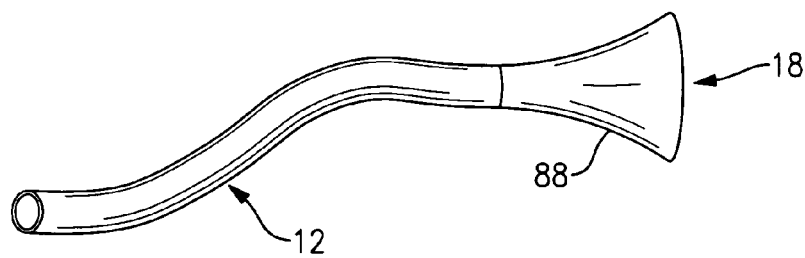

As shown in FIG. 2G, the insertion tube 12 may further include a strain relief member 88. The strain relief member 88 is a polymeric member that fits over the proximal end 18 of the insertion tube 12 and is coupled to the insertion tube 12. The strain relief member has a variable cross section that gradually decreases from a stiff section adjacent to the proximal end 18 of the insertion tube 12. The strain relief member 88 is configured for engagement with a handset or display (not shown) and serves to prevent a stress concentration where the proximal end 18 is coupled to the handset 16, thereby reducing the stress levels in the insertion tube 12.

FIG. 3 illustrates a top-down view of an insertion tube 140 being transferred into a rotating storage carousel 110. The storage carousel 110 includes a rotatable cavity 150 and apparatus supporting its rotation. In this embodiment, the storage carousel apparatus includes a base 160, a peripheral barrier 120, and a pivot shaft 130 that bound the rotatable cavity 150. The cavity 150 is configured for storing elongated flexible objects, such as an insertion tube 140 of a remote viewing device. Some embodiments of a storage carousel 110 can also be referred to as a reel or a drum. In the illustrative embodiment a force applied to the insertion tube 140 frictionally transfers to the storage carousel 110, and causes it 110 to rotate in the counterclockwise direction. The storage carousel 110 is configured to rotate in both the clockwise and counterclockwise directions.

In this embodiment, the cavity 150 of the storage carousel 110 rotates around a vertical axis of rotation 380 (shown in FIG. 5) that is substantially parallel to the gravitational direction and that is generally coaxial with the pivot shaft 130. The peripheral barrier 120 surrounds the axis of rotation and defines an outer boundary of the cavity 150. The peripheral barrier 120 functions as a retaining wall to hold and store at least one elongated flexible object, such as the insertion tube 140, within the cavity 150.

The profile of the peripheral barrier 120 can be of a cylindrical shape further having a circular or non-circular shaped cross-section. Or, the profile of the peripheral barrier 120 can be of an axi-symmetrical shape, such as for example, a cone shape (See FIG. 7A). For example, the profile of the peripheral barrier can be of a circular or polygon shape, such as a triangular, square, hexagonal, or as shown, an octagonal shape. A polygon profile can cause more effective friction between an inner surface of the peripheral barrier and an insertion tube coiled and stored within the cavity surrounded by the peripheral barrier. One of ordinary skill will appreciate that the peripheral barrier 120 can be of any shape that can function as an effective retaining wall for an elongated flexible object, such as an insertion tube 140 stored within the cavity 150.

The base 160 functions as a retaining floor to support and hold at least one stored elongated flexible object, such as an insertion tube 140, within the cavity 150. In this embodiment, the base 160 is disposed substantially perpendicular, and is fixedly attached to, the pivot shaft 130 and rotates with the pivot shaft 130. In other embodiments, the base 160 is rotatably attached to the pivot shaft 130 while the pivot shaft 130 is fixedly attached to the frame 260.

As shown, a force is applied to the insertion tube 140 that effectively pushes the insertion tube 140 into the storage carousel 110. In response, the force applied to the insertion tube 140 is transferred and directed generally tangential to the perimeter of the storage carousel 110, applying a rotational force that causes the storage carousel 110 to rotate in a counter clockwise direction.

In some embodiments, the peripheral barrier 120 and/or the base 160 is constructed in a manner that prevents slipping and that aids in the transfer of force between an insertion tube 140 and the carousel 110. For example, the peripheral barrier 120 and/or the base 160 can be constructed with friction pads or ribs which provide resistance to slipping at points of contact between the insertion tube 140 and the peripheral barrier 120 and/or the base 160.

Figure 7A:
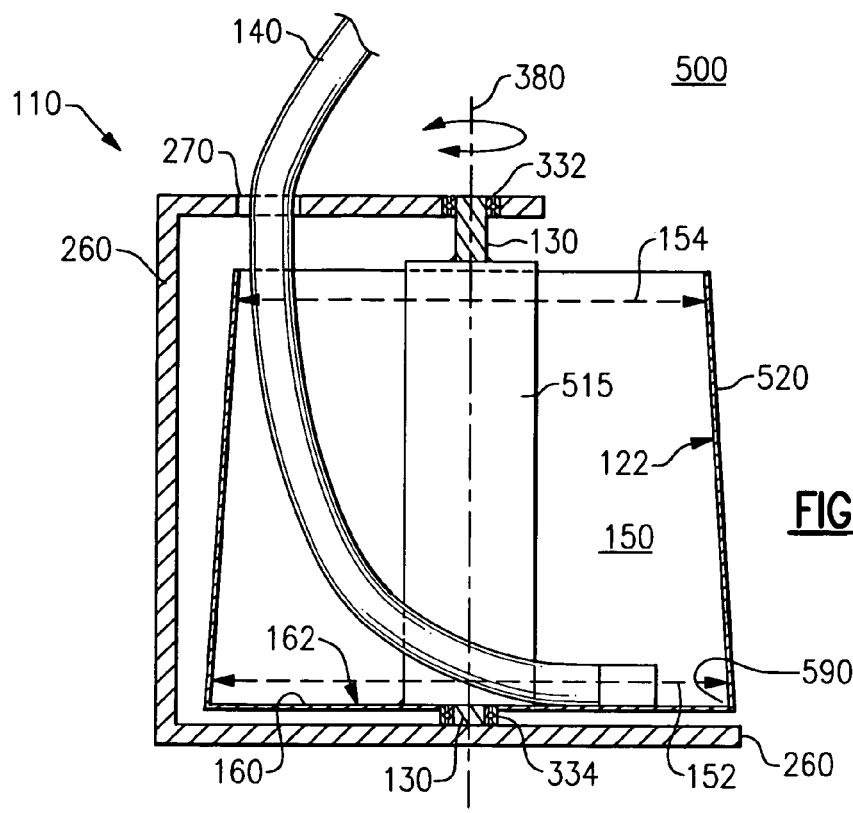
FIG. 7A illustrates a side cross-sectional view of an embodiment of the storage carousel having a vertical axis of rotation and a cone shaped peripheral barrier that surrounds a hub.
Figure 7B:
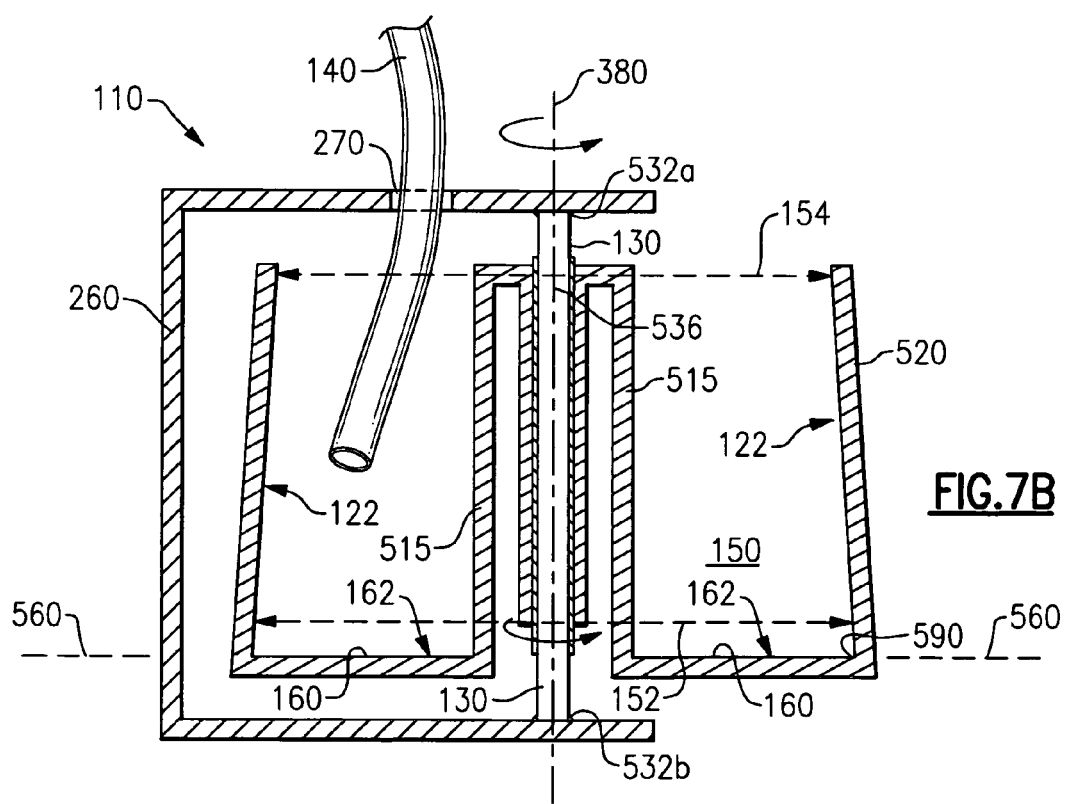
FIG. 7B illustrates a side cross-sectional view of an embodiment of the storage carousel like that of FIG. 7A but that is rotatably attached to the pivot shaft.

As illustrated in FIGS. 7A and 7B, a cone-shaped peripheral barrier provides an acute angle shaped corner, having less than a 90 degree angle, located at the intersection of the peripheral barrier 520 and the base 160. The acute angle shaped corner creates more resistance to slipping of the insertion tube 140 than is provided by a 90 degree angle between the peripheral barrier 120 and the base 160.

Figure 5:
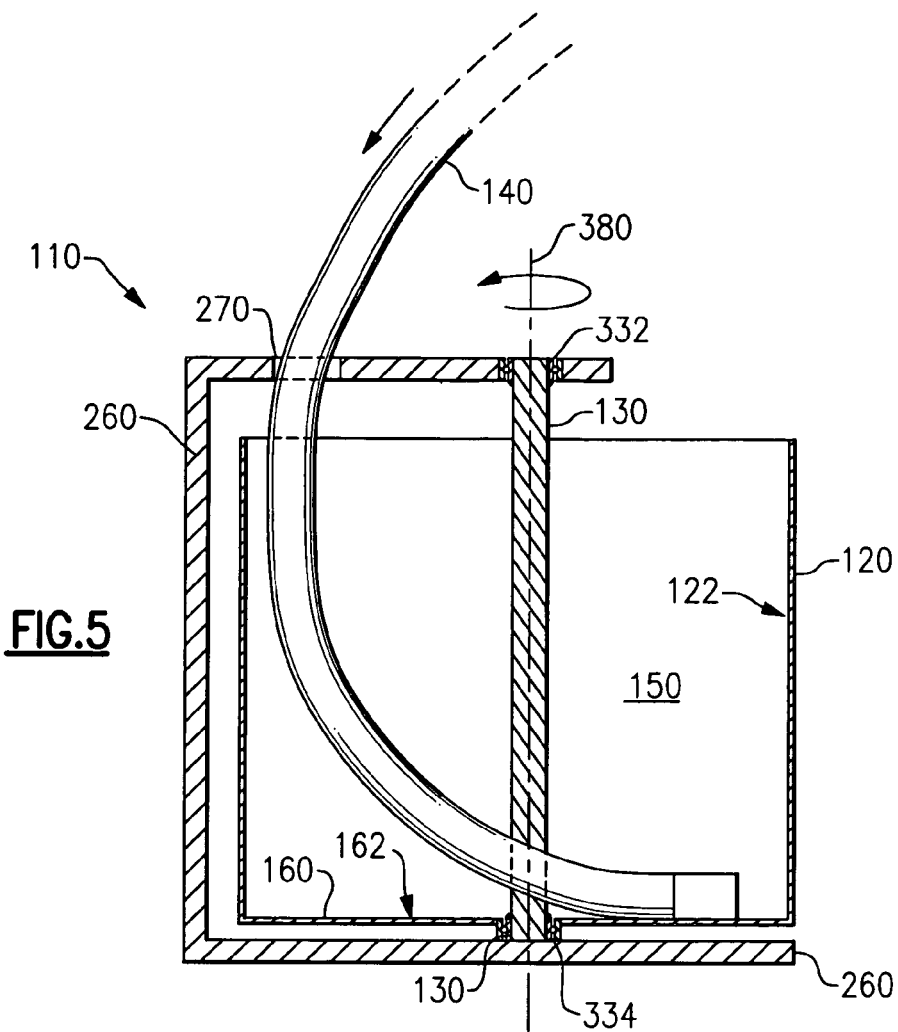
FIG. 5 illustrates a side cross-sectional view of the illustration of FIG. 4 showing a larger portion of the frame.

As shown, a portion of the insertion tube 140 that is stored within the cavity 150 is disposed around the pivot shaft 130 and disposed adjacent to an inner wall of the peripheral barrier 120 that bounds the cavity 150. The insertion tube is transferred to the carousel both circumferentially (FIG. 3) and/or axially (FIG. 5). During the transfer of the insertion tube 140 into the cavity 150, additional portions of the insertion tube 140 that enter the cavity 150 are disposed on top of previous portions of the insertion tube and are stored adjacent to the inner wall of the peripheral barrier 120. The peripheral barrier 120 retains the insertion tube 140 within the cavity 150.

Preferably, any elongated and flexible object to be stored into the carousel, such as the insertion tube 140 that possesses sufficient rigidity to allow it 140 to be pushed into the storage carousel 110. The rigidity of such an object stored within the cavity causes a resistance to coiling that manifests by the object generating a radial uncoiling force that presses away from the pivot shaft 130 and against the inner side of the peripheral barrier 120. The peripheral barrier 120 is configured with sufficient strength to counteract such a radial uncoiling force and to retain the object, such as an insertion tube 140, within the cavity 150.

The insertion tube 140 is removed from the storage carousel 110 by simply pulling it out of the cavity 150. The pulling force applied to the insertion tube 140 stored within the cavity 150 transfers and applies a force to the storage carousel 110, causing it to rotate in an opposite (clockwise) direction.

In this embodiment the pivot shaft 130 is rotatably attached to the frame 260 (FIG. 5) and fixedly attached to the base 160. In other embodiments, the pivot shaft 130 is rigidly attached to the frame 260 while the base 160 and the peripheral barrier 120 are rotatably attached to, and rotate around, the pivot shaft 130.

In other embodiments, the storage carousel 110 does not include a pivot shaft 130 and the base 160 rotates using means that exclude a pivot shaft 130. The means that exclude a pivot shaft 130 can include the employment of ball bearings or a circular track disposed on a lower side of the base 160 (not shown). In yet other embodiments, the cavity 150 of the storage carousel 110 rotates in response to a force generated by a motor.

Disposing an elongated and flexible object into a coil can substantially reduce the dimensions required to store such an object. For example, an insertion tube of 25 feet in length and approximately a third of an inch in diameter and can be coiled into a cylindrical volume of approximately 15 inches in diameter and length. Unfortunately, some elongated and flexible objects, such as an insertion tubes, resist coiling. Disposing such an object into a coiled arrangement causes the object to generate an uncoiling force that can interfere with its convenient and efficient storage. The apparatus of the invention addresses this problem by storing an object along an inner surface of the apparatus.

FIG. 4A illustrates a top-down view of the embodiment of FIG. 3 further including a frame 260 and an insertion port 270. An insertion port is also referred to herein as an entryway. As shown, only a portion of the frame 260 is visible from the top-down view perspective. The remaining portion of the frame 260, not visible from this perspective, resides substantially parallel to and below the peripheral barrier 120.

As shown, the insertion port 270 is embodied as a passageway through the frame 260. As shown, the passageway embodying the insertion port 270 has a substantially circular shape. Preferably, the insertion port 270 is shaped, sized and located to allow passage of an elongated and flexible object, such as an insertion tube 140, into and out of the cavity 150 with minimum applied force to the object.

FIG. 4B illustrates another embodiment of the invention of FIG. 4A further including an angled inlet tube 272. The angled inlet tube 272 that is disposed adjacent to the passageway of the insertion port 270 is configured to further guide the passage of an insertion tube 140 into and out of the cavity 150. The angled inlet tube 272 provides an elongated cavity through which an insertion tube 140 can pass into an out of the cavity 150.

In this embodiment, the pivot shaft 130 is attached to the base 160 and rotatably attached to the frame 260. In alternative embodiments, the pivot shaft 130 is rigidly attached to the frame 260 and rotatably attached to the base 160. In the subject embodiment, the peripheral barrier 120 and the base 160 rotate with the pivot shaft 130.

FIG. 4C illustrates a variation of the embodiment of FIG. 4A further including a partial base plate. In this embodiment, the partial base plate forms a horizontal rim 266 located along the bottom of the peripheral barrier 120 that supports the stored insertion tube 140 from gravity like a full base plate 160. Optionally, the partial base plate 266 is attached to the pivot shaft 130 via spoke-like structural members 268a, 268b and 268c.

FIG. 5 illustrates a side cross-sectional view of the illustration of FIG. 4A showing a larger portion of the frame 260. As shown, portions of the frame 260 reside above, below and substantially parallel to one side of the peripheral barrier 120. The portions of the frame 260 residing above and below the peripheral barrier 120 are substantially parallel to the base 160 of the storage carousel 110.

As shown, the rotational axis 380 is coaxial with the longitudinal axis of the pivot shaft 130 of the storage carousel 110. In this embodiment, the pivot shaft 130 is fixedly attached to the base 160 and rotatably attached to the frame 260 at its top connection 332 and at its bottom connection 334. An insertion tube 140 is shown being transferred through the insertion port 270.

The base 160 has an inner surface 162 that is configured to make frictional contact with the insertion tube 140. Likewise, the peripheral barrier 120 has an inner surface 122 that is configured to make frictional contact with the insertion tube 140. In some embodiments, the peripheral barrier 120 and/or the base 160 are constructed with friction pads (not shown) to provide substantial inner surface (122, 162) friction between the insertion tube 140 and the peripheral barrier 120 and/or the base 160.

In some embodiments, the peripheral barrier 120 and/or the base 160 is constructed with ribs (not shown) which provide resistance to slipping at points of contact between the insertion tube 140 and the peripheral barrier 120 and/or the base 160 respectively. In particular, expansion forces that resist coiling of the insertion tube 140 create a pressing force against the ribs within a peripheral barrier 122. The pressing force can produce a substantial frictional force between the ribs of the peripheral barrier 120 and the insertion tube 140. This frictional force can be exploited to force the peripheral barrier and the cavity 150 to rotate in response to the transfer of the insertion tube 140 into or out of the cavity 150.

In other embodiments, a portion of the frame 260 does not reside below the base 160 and instead, the base resides on ball bearings or a track, and rotates without any other attachment to the bottom portion of the frame 260.

Figure 6:
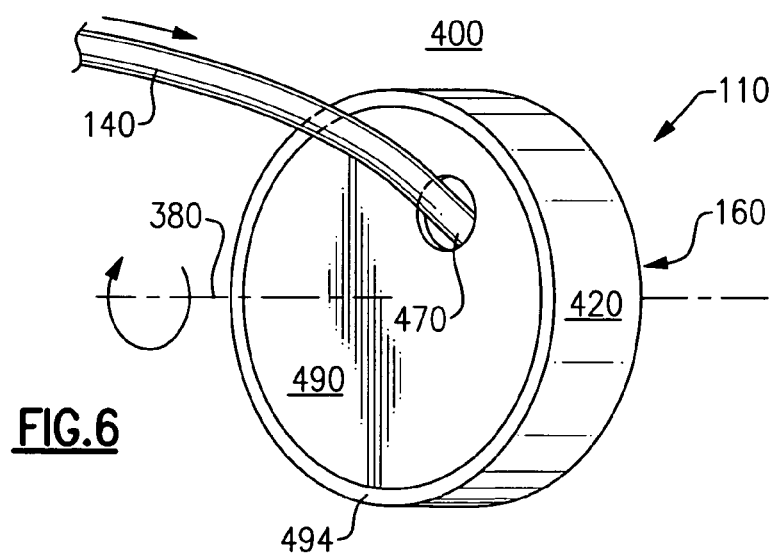
FIG. 6 illustrates a wall mountable embodiment of the invention having a vertical orientation, a horizontal axis of rotation and a cover plate that includes an insertion port.

FIG. 6 illustrates a wall mountable embodiment of the invention 400 having a vertical orientation, a horizontal axis of rotation 380 and a cover plate 490 that includes an insertion port 470. The cover plate 490 and the base plate 160 are also both referred to as end plates. In this embodiment, the axis of rotation 380 is substantially horizontal and substantially perpendicular to the direction of gravity.

The cover plate 490 is stationary and is not attached to the peripheral barrier (not shown) that rotates inside of an outer casing 420 during the transfer of an object into or out of the cavity 150 (shown in FIG. 5). The cover plate 490 includes an insertion port 470. Unlike the insertion port 270 of FIG. 4A, the insertion port 470 of FIG. 6 is embodied as a passageway through the cover plate 490. As shown, the opening of the passageway of the insertion port 470 is of a circular shape. In other embodiments, the opening of the passageway of the insertion port 470 can be of other shapes.

As shown, an elongated object, specifically an insertion tube 140, is being transferred into the storage carousel 400 through the insertion port 470. As shown, a radial gap 494 exists between the cover plate 490 and the outer casing 420. To prevent contact between the stationary cover plate 490 and the rotating peripheral barrier (not shown), a gap (not shown) exists between the cover plate 490 and the rotating peripheral barrier which rotates inside of the outer casing 420. Optionally, a stationary surface (not shown) attached to the frame and disposed outside of the base 160 (not shown) is adapted for wall mounting using various and well known attachment mechanisms.

Insertion tubes 140 can be used for inspecting within potentially radioactive environments. For example, an insertion tube 140 can be used to inspect heat exchange tubes within a steam generator of a nuclear power plant. Each heat exchange tube is designed to carry radioactive coolant that causes radioactive contamination to the inner surface of each heat exchange tube. Passing an insertion tube through a radioactive heat exchange tube will cause radioactive contamination to the insertion tube 140. Likewise, storing a radioactively contaminated insertion tube into a storage carousel will cause radioactive contamination to the storage carousel 110.

To address this type of problem, in some embodiments, the storage carousel 110 is designed to be removable from other remote viewing device components and to be hand carried (portable) by a user of a remote viewing device. For this type of embodiment, the contaminated insertion tube is only stored within an associated and contaminated storage carousel 110.

FIG. 7A illustrates a cross-sectional view of an embodiment of the storage carousel 110 having a vertical axis of rotation 380 and a cone shaped peripheral barrier 520 that surrounds a hub 515. A longitudinal axis of the pivot shaft 130 and of the hub 515 are each coaxial with the axis of rotation 380. The axis of rotation 380 is substantially vertical (parallel to the direction of gravity). The inner surface of the cone shaped peripheral barrier 520 is angled such that it is not perpendicular to the base 160 and not parallel to the axis of rotation 380 of the storage carousel 110. In this embodiment, the pivot shaft 130 is fixedly attached to the base 160 of the carousel 110 and rotatably attached to the frame 260 at its top connection 332 and at its bottom connection 334. An insertion tube 140 is shown being transferred through the insertion port 270.

A cone shaped peripheral barrier 520 provides an acute angle-shaped corner 590, having an angle of less than a 90 degrees, formed between the peripheral barrier 520 and the base 160. The acute angle shaped corner 590 forms a space that receives an insertion tube 140 in a manner that provides more resistance to slipping of the insertion tube 140 than that provided by a 90 degree angle between the peripheral barrier 120 and the base 160.

Furthermore, a cone shaped peripheral barrier 520 also reduces the likelihood of tangling an insertion tube 140 stored within the cavity 150. Within a cavity 150 having a cone shaped peripheral barrier 520, the maximum diameter of the cavity 150 is located along the inner surface of the cone shaped peripheral barrier 520 that is adjacent (most proximate) to the base 160 (at the acute angle shaped corner 590) and the minimum diameter of the cavity 150 is located along the inner surface of the cone shaped peripheral barrier 520 that is farthest from the base 160. As shown, a larger diameter 152 is located proximate to the base 160 and a smaller diameter 154 is located farther from the base 160. The diameter of the cavity 150 continually reduces along the inner surface of the cone shaped peripheral barrier 520 from its maximum to its minimum value.

The radial uncoiling force of an insertion tube 140 causes the coil diameter of the insertion tube 140 to expand to the largest diameter permitted by the shape of the cavity 150. Consequently, the radial uncoiling force of an insertion tube 140 causes it to press against and slide along inner surface of the cone shaped peripheral barrier 520 (if necessary) in order for it 140 to first coil at the largest diameter adjacent to the base 160 of the cavity 150. While being continuously transferred into the cavity 150, the insertion tube 140 further coils and stacks within the cavity 150 along the inner surface of the cone shaped peripheral barrier 520 in a direction away from the base 160. The coiling and stacking of the insertion tube 140 in this manner reduces the likelihood of tangling the insertion tube 140 when transferring it 140 to and from the cavity 150.

The pivot shaft 130 and the hub 515 are cylindrical in shape. The hub 515 has a wider profile (larger diameter) than that of the pivot shaft 130 and displaces more space within the center of the cavity 150 as compared to the space displaced by the pivot shaft 130 alone. The wider profile of the hub 515 results in a more annular shaped cavity 150 that reduces the likelihood of entanglement and better accommodates the transfer of the insertion tube 140 into the cavity 150.

During withdrawal of the insertion tube from the carousel 110, the wider hub 515 causes the pulling force upon an insertion tube 140 stored within the cavity 150 to transfer to the carousel 500 at a radial location that is at least a minimum distance away from the rotational axis 380 of the carousel 500, effecting a more tangential force to the carousel 500. In particular, the outer diameter (OD) of the hub 515 prevents the insertion tube from being pulled across the center of the cavity 150 during the withdrawal of the insertion tube.

FIG. 7B illustrates a side cross-sectional view of an embodiment of the storage carousel 110 like that of FIG. 7A but that is rotatably attached to the pivot shaft 130. Unlike the embodiment shown in FIG. 7A, the base 160 of the carousel 110 is rotatably attached to the pivot shaft 130 at location 536 while the pivot shaft 130 is fixedly attached to the frame 260 at locations 532a and 532b.

As shown, the peripheral barrier 520, base 160 and the hub 515 are attached as one piece and are rotatably attached to the pivot shaft 130. The pivot shaft is fixedly attached to the frame at locations 532a and 532b. Like other embodiments of the invention, the inner side of the base 160 is a planar surface that defines a plane 560 which intersects the axis of rotation 380. Like shown in FIG. 7A, a larger diameter 152 of the rotatable cavity 150 is located proximate to the base 160 and a smaller diameter 154 of the rotatable cavity 150 is located farther from the base 160.

Figure 8A:
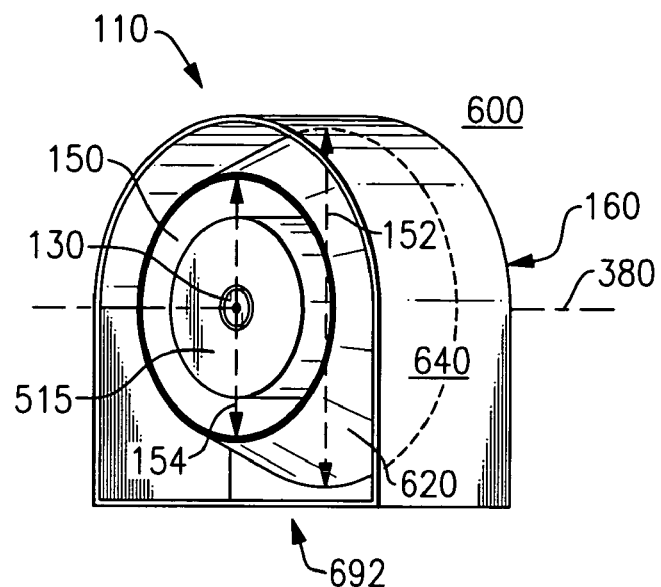
FIGS. 8A-8B illustrate a floor-standing embodiment of the invention having a vertical orientation, a horizontal axis of rotation and an outer casing that includes a cover plate and a flat bottom support surface.
Figure 8B:
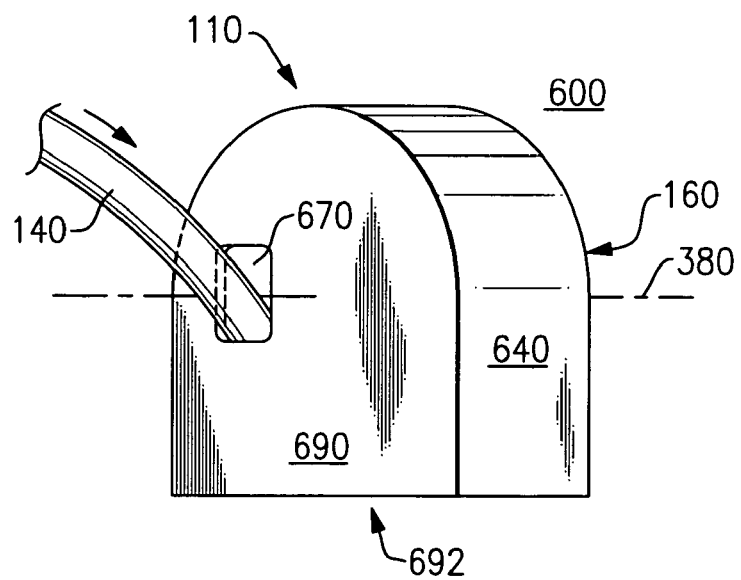

FIGS. 8A and 8B illustrate a preferred floor standing embodiment of the invention 110 having a vertical orientation, a horizontal axis of rotation 380 and an outer casing 640 that includes the cover plate 690 and a flat bottom support surface 692. While disposed in a floor standing position, the storage carousel 110 rests on the flat bottom support surface 692.

Referring to FIG. 8A, the outer casing 640 excludes the cover plate 690 and is shown to enclose the peripheral barrier 620. Note that the cover plate 690 is shown in FIG. 8B. The peripheral barrier 620 surrounds the pivot shaft 130 and the hub 515 and has a cone shape, like that of the peripheral barrier 520 shown in FIGS. 7A and 7B. The axis of rotation 380 is coaxial with the longitudinal axis of the pivot shaft 130 and of the hub 515. The pivot shaft 130 and the hub 515 are both cylindrical in shape. In this embodiment, like FIG. 7B, the base 160 is rotatably attached to the pivot shaft 130 while the pivot shaft 130 is fixedly attached to the frame 260.

The cavity 150 bounded by the cone-shaped peripheral barrier 620 is annular in shape. The cone shaped peripheral barrier bounding the cavity 150 creates a larger diameter annular storage space towards the base 160 (not shown) as compared to that of the storage space available farther away from the base 160 and towards the cover plate 690, shown in FIG. 8B.

A cone shaped peripheral barrier 620 provides an acute angle-shaped corner (not shown), like the acute angle shaped corner 590 shown in FIGS. 7A and 7B, of less than a 90 degree angle, formed between the peripheral barrier 620 and the base (not shown). The acute angle shaped corner forms a space that creates more resistance to slipping of the insertion tube 140 than that provided by a 90 degree angle between the peripheral barrier and the base. Like shown in FIGS. 7A and 7B, a larger diameter 152 of the rotatable cavity 150 is located proximate to the base 160 and a smaller diameter 154 of the rotatable cavity 150 is located farther from the base 160.

Referring to FIG. 8B, the outer casing 640 includes a cover plate 690 (not shown in FIG. 8A) including an insertion port 670. Optionally, a stationary surface (not shown) that is disposed outside of the base 160 can be adapted to accommodate wall mounting of this embodiment of the storage carousel 110.

In some embodiments, the angled inlet tube 272 (shown in FIG. 4B) is attached to the cover plate 690 at a location over the insertion port 670. In this type of embodiment, the angled inlet tube 272 is detachable from the cover plate 690 in manner that exposes an opening (not shown) in the cover plate 690.

The opening allows for access and service to the inner portions of the carousel 110. Through this opening (not shown), contents of the carousel 110, such as an insertion tube 140, can be untangled (if necessary) and removed from the cavity 150. Additionally, inner portions of the carousel, including the hub 515, the base (not shown) and the peripheral barrier 620 can be cleaned.

Like other embodiments of the invention, pushing and inserting an object, such as an insertion tube, through the inlet port 670 and into the cavity 150 causes the storage carousel 110 to rotate in a first direction. While rotating, the storage carousel 110 accommodates receiving the object for storage into the cavity 150 along the inner side of the peripheral barrier 620.

Likewise, pulling an object, such as an insertion tube, from the cavity 150 and through the inlet port 670, causes the storage carousel 110 to rotate in a second direction opposite from the first direction. While rotating, the storage carousel 110 accommodates the discharge of the object from the cavity 150 through the inlet port 670.

In some embodiments, a passageway forming an insertion port is sized and shaped to accommodate the passage and storage of a once-folded elongated flexible object. In this type of embodiment, an elongated flexible object, such as an insertion tube 140, is folded in half at a location proximate to the middle of the elongated flexible object. The folded portion of the elongated flexible object is first passed through the insertion port 670. The insertion port 670 is sized to be sufficiently large to accommodate the smallest bend radius of the elongated flexible object.

One advantage of this type of embodiment is that, the storage time for transferring an object can be reduced to half. Furthermore, when storing a folded insertion tube 140, the viewing head of the insertion tube 140 is the last portion of the insertion tube 140 to transfer into the carousel 110 and the first portion of the insertion tube 140 to be removed from the carousel 110. In this embodiment, the viewing head can be inspected or replaced without fully removing the insertion tube 140 from the storage carousel 110.

As previously stated, the radial uncoiling force of an insertion tube 140 causes the coil diameter of the insertion tube 140 to expand to the largest diameter permitted by the shape of the cavity 150. Consequently, the radial uncoiling force of an insertion tube 140 causes it to press against and slide along inner surface of the cone shaped peripheral barrier 520 (if necessary) (See FIG. 7) in order for it 140 to first coil at the largest diameter adjacent to the base 160 of the cavity 150.

While being continuously transferred into the cavity 150, the insertion tube 140 further coils and stacks within the cavity 150 along the inner surface of the cone shaped peripheral barrier 520, 620 in a direction away from the base 160. The coiling and stacking of the insertion tube 140 in this manner reduces the likelihood of tangling the insertion tube 140 when transferring it 140 to and from the cavity 150.

The pivot shaft 130 and the hub 515 are shown as being cylindrical in shape, although the hub 515 can have a conical shape similar to that of the peripheral barrier 620. The hub 515 has a wider profile (larger diameter) than that of the pivot shaft 130 and displaces more space within the center of the cavity 150 as compared to the space displaced by the pivot shaft 130 alone. The wider profile of the hub 515 results in a more annular shaped cavity 150 that reduces the likelihood of entanglement and better accommodates the transfer of the insertion tube 140 into the cavity 150.

During withdrawal of the insertion tube from the carousel, the wider hub 515 causes the pulling force upon an insertion tube 140 stored within the cavity 150 to transfer to the carousel 500, 600 at a radial location that is at least a minimum distance away from the rotational axis 380 of the carousel 500, 600, effecting a more tangential force to the carousel 500, 600. In particular, the outer diameter (OD) of the hub 515 restrains the location of the insertion tube and prevents the insertion tube from being pulled across and proximate to the center of the cavity 150 during the withdrawal of the insertion tube.

Figure 9A:
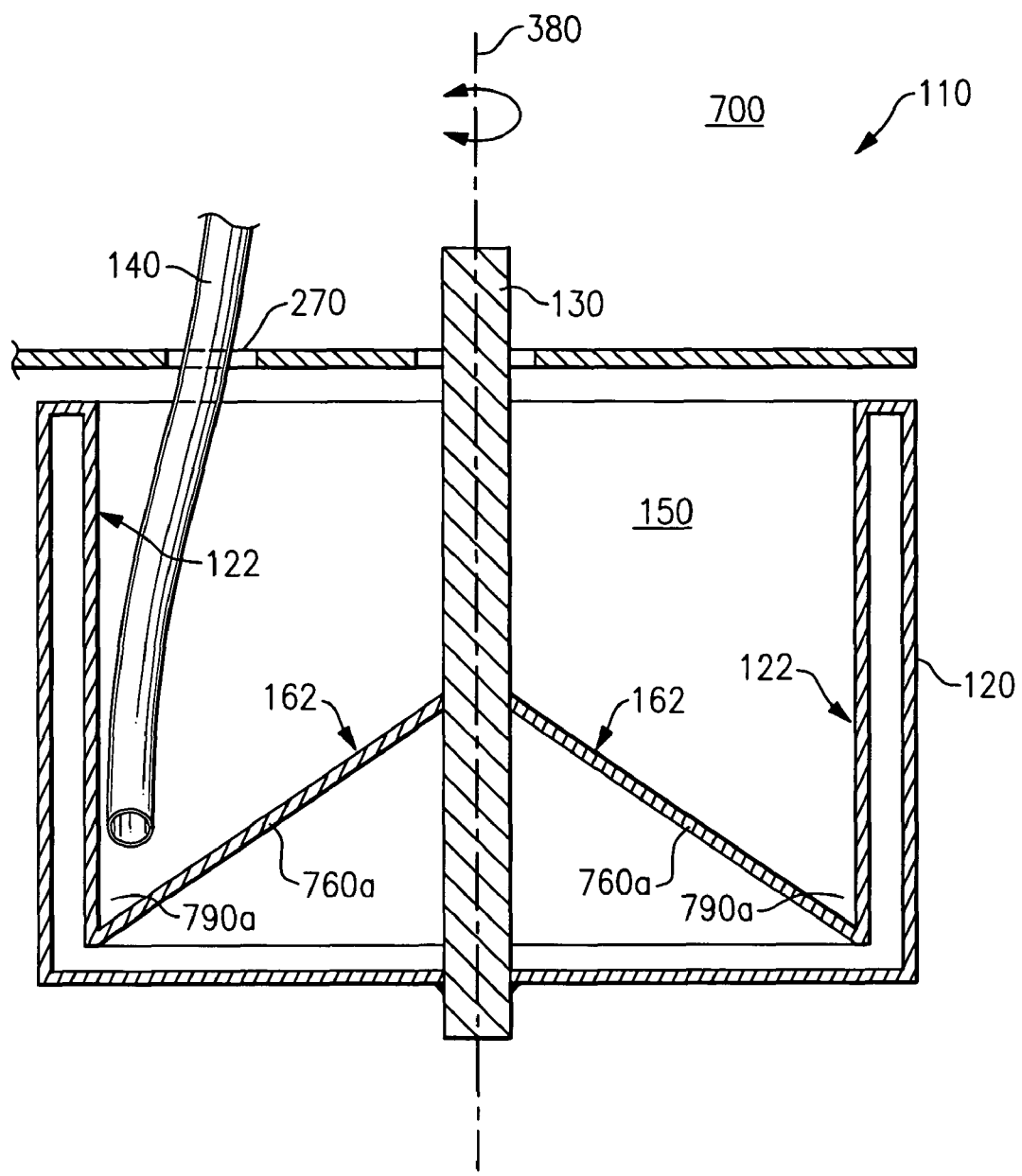
FIGS. 9A-9C illustrate multiple embodiments of the invention including an angled base that is not substantially perpendicular to the rotational axis.
Figure 9B:
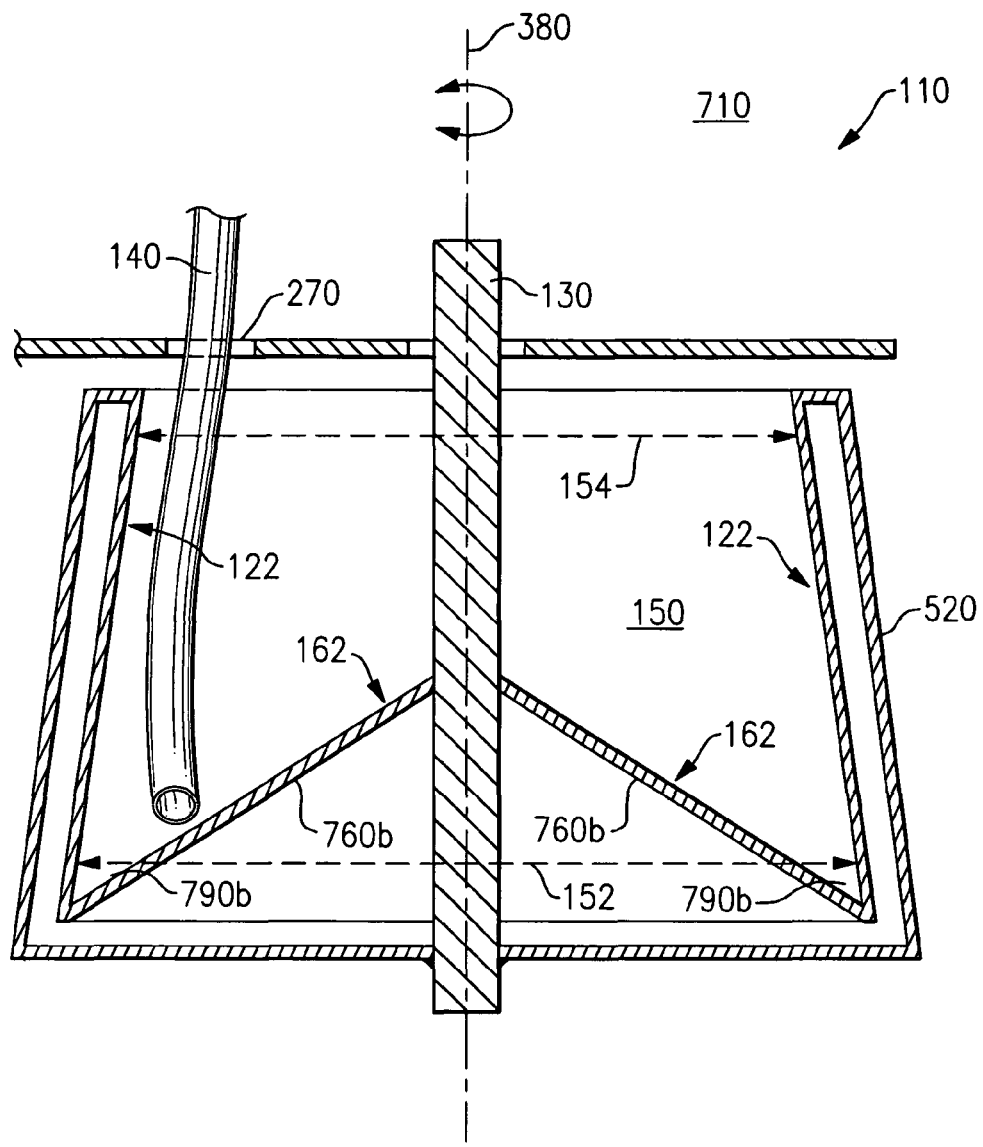
Figure 9C:
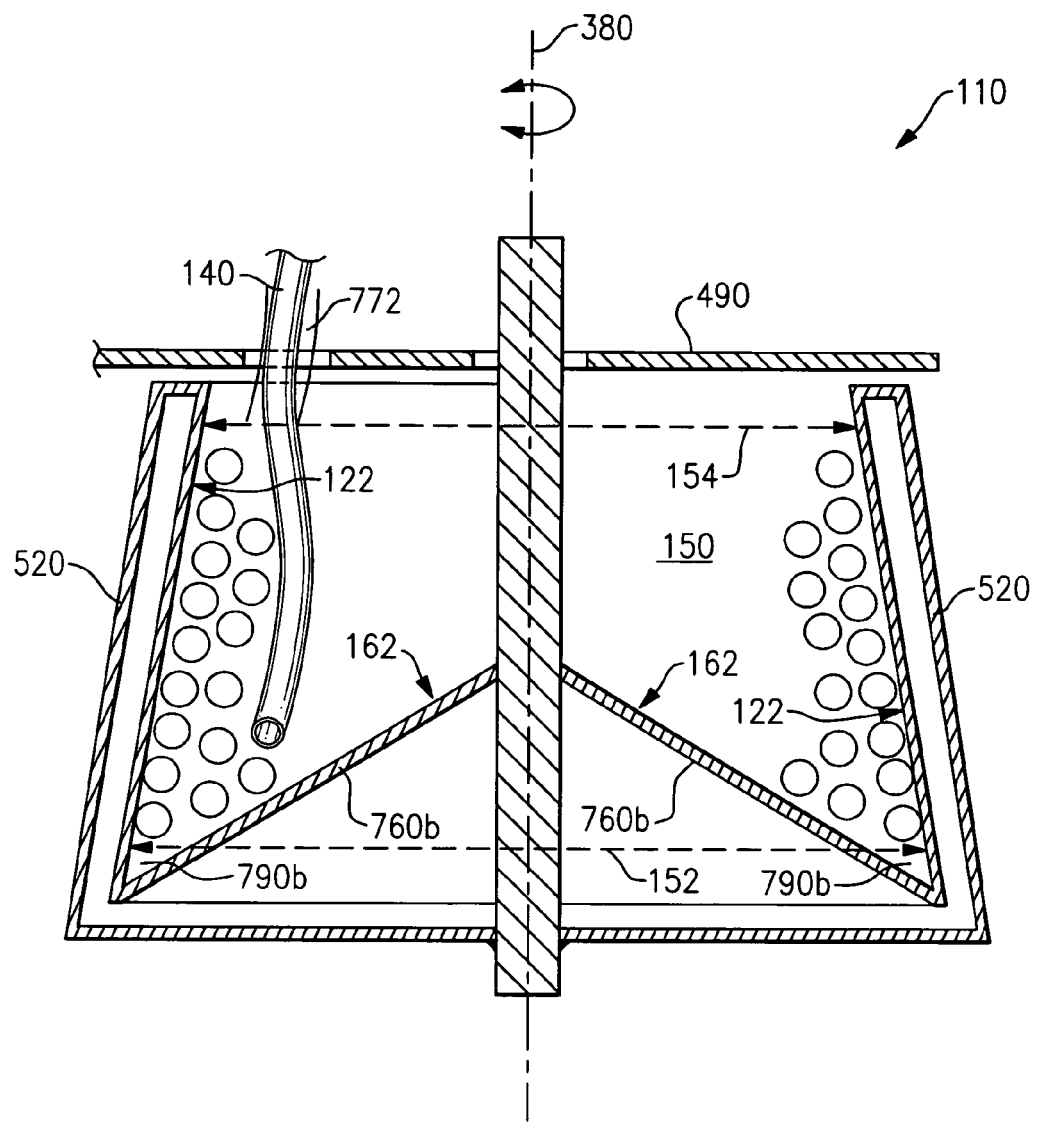

FIGS. 9A-9C illustrate a cross-sectional view of embodiments of the invention including angled bases 760a and 760b. As shown in FIG. 9A, the axis of rotation 380 is substantially vertical. The inner surface of the cone shaped peripheral barrier 120 is vertical and parallel to the axis of rotation 380 of the storage carousel 110.

FIG. 9A illustrates a cross-sectional view of the embodiment of the invention 700 including an angled base 760a that is not substantially perpendicular to the axis of rotation 380. The angled base 760a, like the cone shaped peripheral barrier 520 of FIGS. 7A and 7B, provides an acute angle shaped corner 790a, of less than a 90 degree angle, formed between the peripheral barrier 120 and the base 760a. The acute angle shaped corner 790a forms a space that receives an insertion tube 140 in a manner that provides more resistance to slipping of the insertion tube 140 than that provided by a 90 degree angle between the peripheral barrier 120 and the base 760a.

FIG. 9B illustrates a cross-sectional view of the embodiment of the invention 710 including an angled base 760b and a cone shaped peripheral barrier 520. Note that the slope of the angled base 760b is less than that of the angled base 760a of FIG. 9A. The combination of the angled base 760b and the cone shaped peripheral barrier 520 provides an acute angle shaped corner 790b, of less than a 90 degree angle, formed between the peripheral barrier 520 and the base 760b. Like shown in FIGS. 7A, 7B and 8A, a larger diameter 152 of the rotatable cavity 150 is located proximate to the base 160 and a smaller diameter 154 of the rotatable cavity 150 is located farther from the base 160.

Note that the size of the angle of the acute angle shaped corner 790b is less than that of the angle of the acute angle shaped corner 790a of FIG. 9A. The acute angle shaped corner 790b forms a space that receives an insertion tube 140 in a manner that provides more resistance to slipping of the insertion tube 140 than that provided by a 90 degree angle between the peripheral barrier 120 and the base 160 of FIG. 5.

FIG. 9C illustrates a cross-sectional view of the embodiment of the invention 710 of FIG. 9B including an angled inlet tube 772. As shown, the angled inlet tube 772 directs an incoming insertion tube 140 towards the inner wall of the peripheral barrier 520. Note that the stored insertion tube 140 forms a layer along the inner wall of the peripheral barrier 520 and then forms other layers stacking away from the inner wall of the peripheral barrier 520. Each layer is formed beginning at the farthest location away from the cover plate 490 and ending at the location nearest the cover plate 490. A new layer is formed when the forming of the previous layer reaches the inside of the cover plate 490.

Figure 10A:
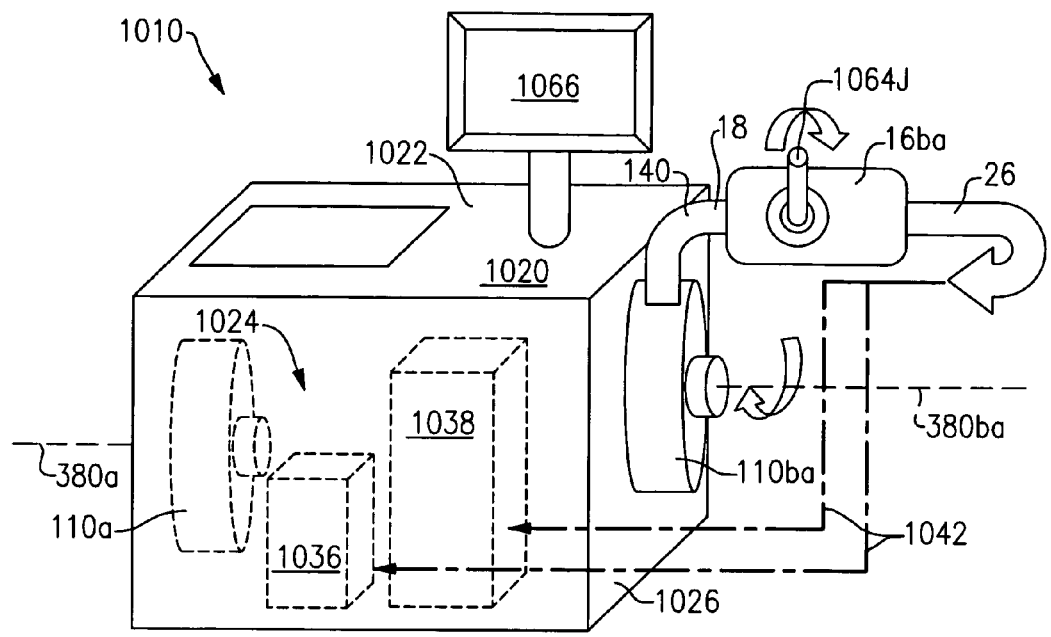
FIGS. 10A-10C illustrate multiple embodiments of the invention providing different locations for disposing the storage carousel with respect to the location of a case for storing endoscope components.
Figure 10C:
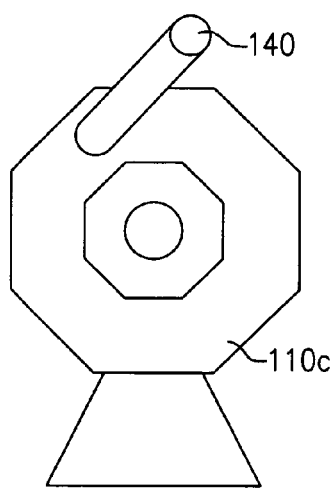
Figure 10B:
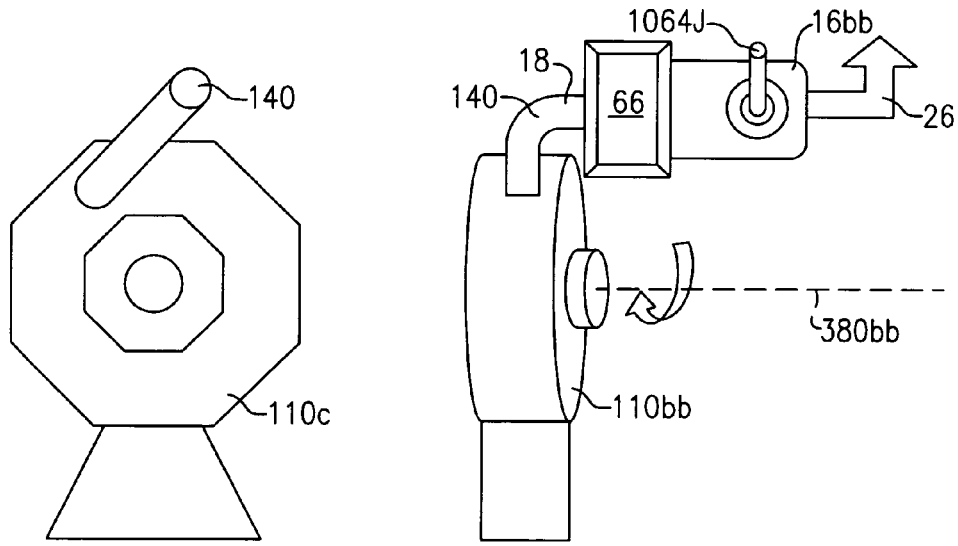

FIGS. 10A-10C illustrate variations of an embodiment 1010 of the insertion tube remote viewing device 10 (See FIGS. 1A-2G) that include a case 1020 and an insertion tube carousel 110a-110c that is positioned at different locations relative to the location of the case 1020. The case 1020 has a generally rectangular shape and an interior cavity 1024 that can be used for storage of components of the insertion tube remote viewing device 1010. As shown, an embodiment of a display 1066 is disposed onto the top surface 1022 of the case 1020 of the remote viewing device 1010.

Referring to FIG. 10A, the interior cavity 1024 of the case 1020 is shown to include a light (illumination) box 1036, an image and data processing module 1038 and an insertion tube storage carousel 110a. The case 1020 has a top surface 1022 attached to an optional hinge (not shown) that can be lifted up to provide access to the interior cavity 1024 of the case 1020.

In this type of embodiment, the insertion tube storage carousel 110a is positioned within the interior cavity 1024 of the case 1020 and rotates around a horizontal axis 380a. An insertion tube 140 can be stored into or removed from the insertion tube storage carousel 110a causing an internal cavity (not shown) of the carousel 10a to rotate around the horizontal axis 380a.

In another type of embodiment, the insertion tube storage carousel 110ba is positioned along a vertical exterior surface 1026 of the case 1020 and rotates around a horizontal axis 380ba. A handset 16ba including a joystick 1064j is shown protruding from the carousel 110ba. Other optional embodiments of the handset 16ba can include an embedded display 66 (FIG. 10B) that is disposed within the handset 16bb. The handset 16ba or 16bb is disposed at a proximal end 18 of an insertion tube 140. A substantial portion of the insertion tube 140, including its distal end (not shown), is stored within an internal rotating cavity (not shown) of the carousel 110ba or 110bb.

Electrical and optical cables 1042 (indicated by a pair of dotted lines) are disposed within an umbilical chord 26 and are electrically and optically connected to the internals of this embodiment of the insertion tube remote viewing device 1010 that include the light (illumination) box 1036 and the image and data processing module 1038.

Referring to FIG. 10B, the insertion tube storage carousel 110bb is shown as detached from and positioned outside of the case 1020 and oriented to rotate around a horizontal axis 380bb. In some embodiments, the storage carousel 110a-110bb is removable from the internal cavity 1024 and/or detachable from the outer surface of the case 1020. Like shown in association with the carousel 110ba, a handset 16bb including a joystick 1064j is shown protruding from the carousel 110bb. The handset 16bb is also disposed at a proximal end 18 of an insertion tube 140 and substantial portion of the insertion tube 140, including its distal end (not shown), is stored within an internal rotating cavity (not shown) of the carousel 110bb.

FIG. 10C illustrates a side view of an embodiment of a storage carousel 110c. As shown, an insertion tube 140 is protruding from the storage carousel 110c. (FIG. 10B). [GEORGE IS TO PROVIDE A REDRAWN FIG. 10C to show the insertion tube existing the carousel from a top, not a side, surface.]

The profile of the storage carousel 110c from the side view has a octagonal shape as opposed to the generally circular shape of the storage carousels 110a-110bb. The storage carousel 110 of the invention is in no way limited to having a circular shape. As shown, embodiments of the insertion tube storage carousel 110a-110c can be configured to be disposed into a variety of positions and locations of the insertion tube remote viewing device 10, 1010 to support the operation of an insertion tube remote viewing device 10, 1010.

Figure 11A:
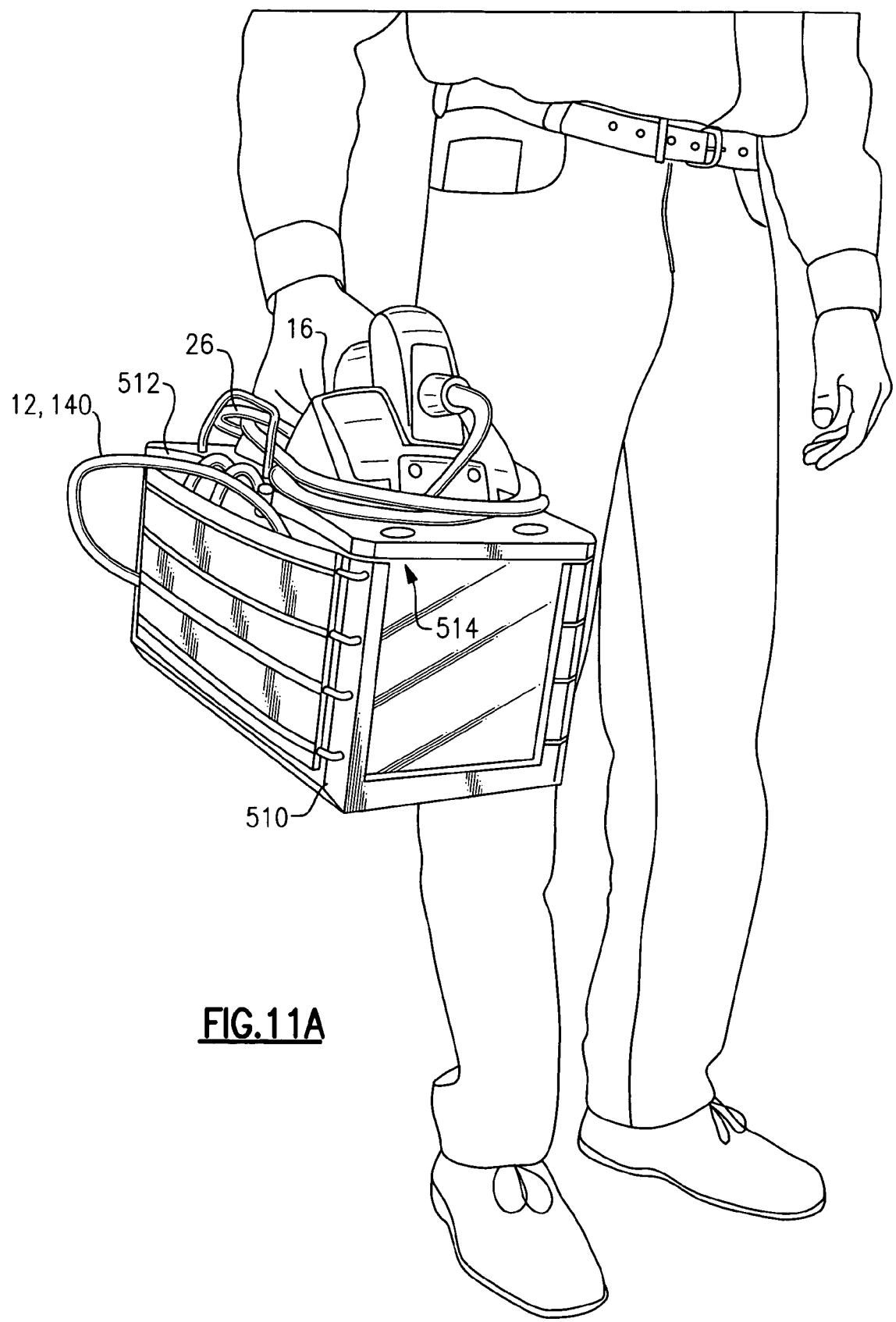
FIG. 11A illustrates and embodiment of the invention including a portable case, also referred to as a portable base module.

FIG. 11A illustrates an embodiment of the invention including a portable case 510, also referred to herein as a base module 510. As shown, a user is carrying the base module 510 by grasping and lifting a handset 16 that is attached to the base module 510. The base module 510 includes a pocket 512 that encloses a portion of an insertion tube 12, 140. An umbilical cord 26 is attached to and wrapped around the handset 16. Alternatively, the user can carry the base module 510 by grasping handles that are proximate to the handset 16.

In this type of embodiment, the insertion tube storage carousel 110 (not shown), 110a (not shown) is located within the interior of the base module 510 and is configured to store at least a portion of the insertion tube 12, 140. An insertion tube 12, 140 is transferred to or from the insertion tube storage carousel 110, 110a causing an internal cavity (not shown) of the insertion tube carousel 110, 110a to rotate around an axis. Preferably, the insertion tube storage carousel 110, 110a rotates around a horizontal axis.

The base module 510 includes at least one first passageway 514 through which at least a portion of the insertion tube 12, 140 can transfer (slide) from outside of the base module 510, into or out of the interior of the base module 510 and into or out of the internal cavity of the insertion tube storage carousel 110, 110a.

Figure 11B:
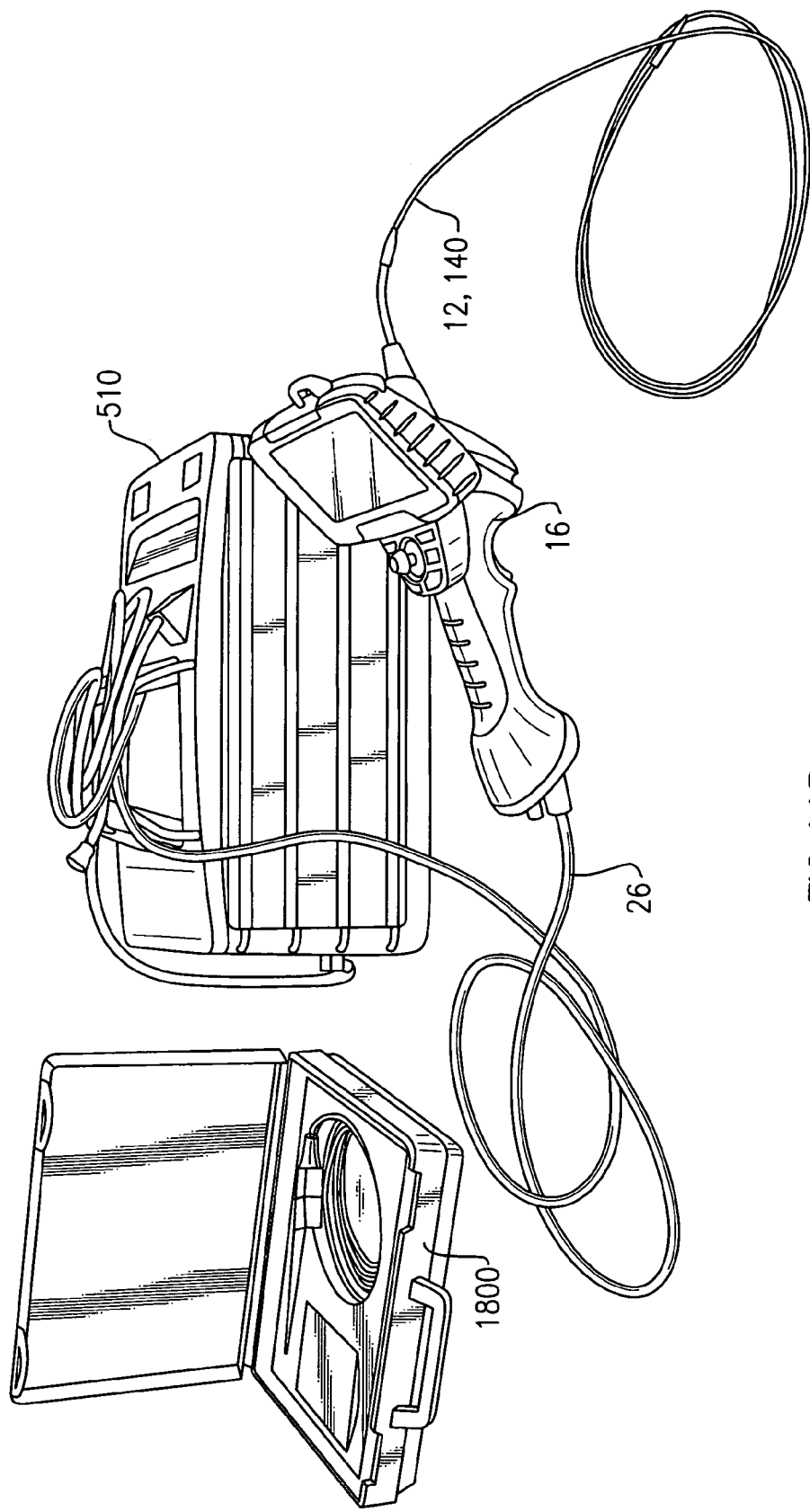
FIG. 11B illustrates a side view of the embodiment of FIG. 11A where the handset is detached from the portable base module.

FIG. 11B illustrates a side view of the embodiment of FIG. 11A where the handset 16 is detached from the base module 510. As shown, the insertion tube 12, 140 remains attached to the handset 16 and but is shown fully withdrawn from the interior of the base module 510. The umbilical cord 26 remains attached to the base module 510. As shown, a spare insertion tube is stored inside of an open storage container 1800.

Figure 12:
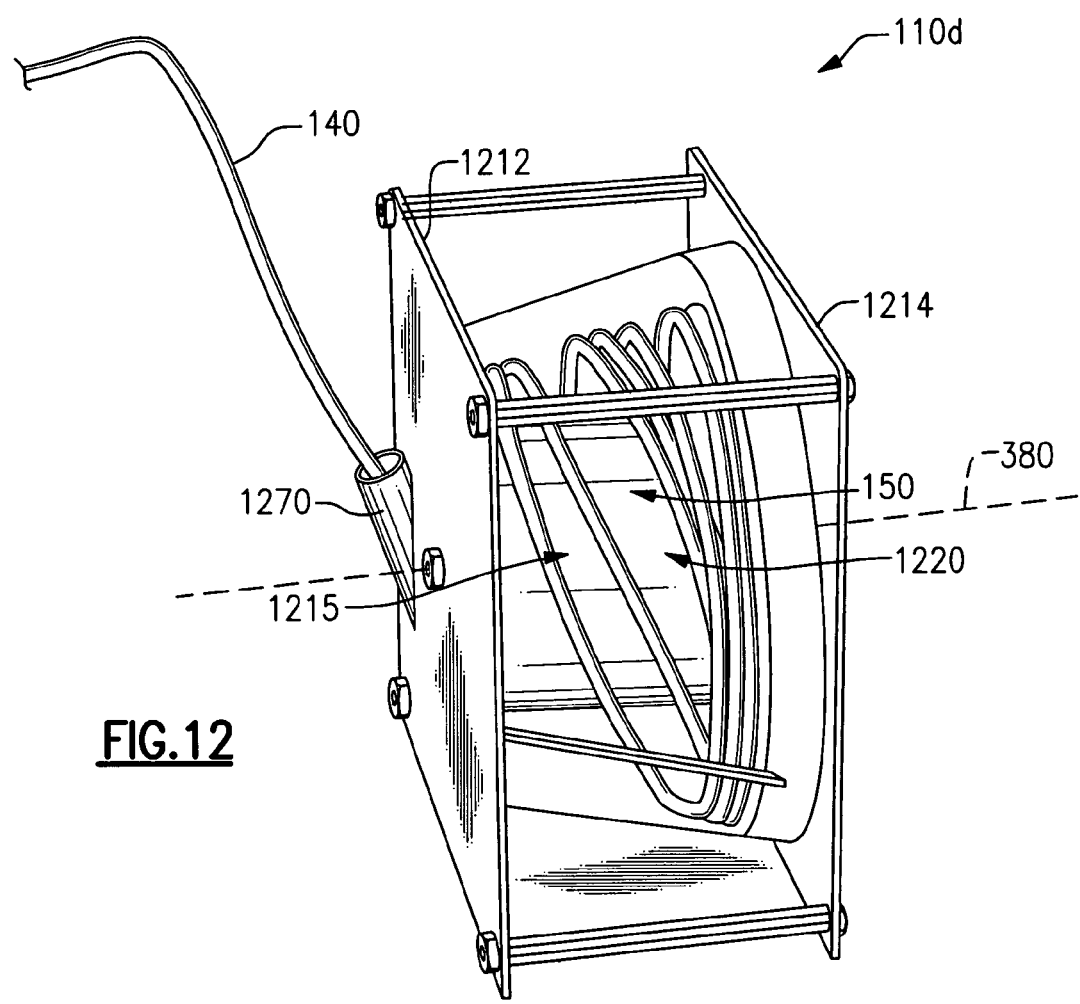
FIG. 12 illustrates an embodiment of the insertion tube carousel including a cone shaped insertion tube storage cavity.

FIG. 12 illustrates an embodiment of the insertion tube carousel 110d including a cone shaped insertion tube storage cavity 150. As shown in this embodiment, the storage cavity 150 is bounded by a transparent-peripheral barrier 1220 and is located between two end plates 1212 and 1214. The cone shaped insertion tube storage cavity 150 is configured to rotate and to store an insertion tube 140. The storage cavity 150 is configured to store a length of insertion tube 140 in a helically wound configuration.

The peripheral barrier 1220 of the insertion tube carousel 110d, which in the embodiment shown comprises a transparent material such as a plastic, is configured to constrain the insertion tube within the storage cavity 150 such as, for example, a right circular cone or a right circular cylinder. The carousel 110 comprises an insertion port 1270 which in this embodiment is a tubular shaped entry fixed to an external surface of an end plate 1212. The insertion port 1270 is aligned with an opening defined in the surface of the endplate 1212. The insertion port 1270 can be conveniently fastened to the end plate 1212 with any conventional fastener, such as with screws.

As shown, the carousel 110d can be conveniently assembled by stacking the required components and holding the endplates 1212, 1214 in place with fasteners, such as with mechanical bolts and interoperating nuts. The rotatable portion of the carousel 10d (e.g. peripheral barrier 1220) is held by mating rotational guides (not shown) to the inner facing surfaces of end plates 1212, 1214. The rotational guides are positioned such that the storage cavity rotates around a rotational axis 380 of the carousel 10d. A rotating hub 1215 is disposed inside of the storage cavity 150. In some embodiments, the base (not shown) and the peripheral barrier 1220 rotate along with the hub 1215.

While the present invention has been particularly shown and described with reference to various modes as illustrated in the drawings, it will be understood by one skilled in the art that various changes in detail may be effected therein without departing from the spirit and scope of the invention as defined by the claims.

We claim:

1. An apparatus for storing an insertion tube of a borescope and endoscope device, said apparatus comprising:
    a storage carousel including a rotatable cavity bounded by at least one inner surface that includes an inner surface of a base and an inner surface of a peripheral barrier, where said rotatable cavity is configured to rotate around an axis of rotation and configured to accommodate storage of an insertion tube having a proximal end and distal end, where said storage is performed without said insertion tube being fixably attached to said storage carousel, and where said storage carousel is configured to allow said proximal end to be located outside of said rotatable cavity while a remaining portion of said insertion tube is stored inside of said rotatable cavity; and
    a frame providing mechanical support to a pivot shaft and including an insertion port, where said insertion port extends through said frame and is configured to guide a transfer of said insertion tube either towards or away from said rotatable cavity;
    where said at least one inner surface is configured to make physical contact and to generate a frictional force between said insertion tube and said at least one inner surface so that said transfer of said insertion tube towards or away from said rotatable cavity causes said rotatable cavity to rotate; and
    where said storage carousel is located within a case, said case storing components of a borescope or endoscope device.

2. An apparatus for storing an insertion tube of a borescope and endoscope device, said apparatus comprising:
    a storage carousel including a rotatable cavity bounded by at least one inner surface that includes an inner surface of a base and an inner surface of a peripheral barrier, where said rotatable cavity is configured to rotate around an axis of rotation and configured to accommodate storage of an insertion tube having a proximal end and distal end, where said storage is performed without said insertion tube being fixably attached to said storage carousel, and where said storage carousel is configured to allow said proximal end to be located outside of said rotatable cavity while a remaining portion of said insertion tube is stored inside of said rotatable cavity; and
    a frame providing mechanical support to a pivot shaft and including an insertion port, where said insertion port extends through said frame and is configured to guide a transfer of said insertion tube either towards or away from said rotatable cavity;
    where said at least one inner surface is configured to make physical contact and to generate a frictional force between said insertion tube and said at least one inner surface so that said transfer of said insertion tube towards or away from said rotatable cavity causes said rotatable cavity to rotate; and
    where said storage carousel is attached to an outer surface of a case, said case storing components of a borescope or endoscope device.

3. An apparatus for storing an insertion tube of a borescope and endoscope device, said apparatus comprising:
    a storage carousel including a rotatable cavity bounded by at least one inner surface that includes an inner surface of a base and an inner surface of a peripheral barrier, where said rotatable cavity is configured to rotate around an axis of rotation and configured to accommodate storage of an insertion tube having a proximal end and distal end, where said storage is performed without said insertion tube being fixably attached to said storage carousel, and where said storage carousel is configured to allow said proximal end to be located outside of said cavity while a remaining portion of said insertion tube is stored inside of said cavity; and
    a frame providing mechanical support to a pivot shaft and including an insertion port, where said insertion port extends through said frame and is configured to guide a transfer of said insertion tube either towards or away from said rotatable cavity;
    where said at least one inner surface is configured to make physical contact and to generate a frictional force between said insertion tube and said at least one inner surface so that said transfer of said insertion tube towards or away from said rotatable cavity causes said rotatable cavity to rotate; and where said storage carousel is located separate from a case, said case storing components of a borescope or endoscope device.

4. An apparatus for storing an insertion tube of a borescope and an endoscope, said apparatus comprising:

a storage carousel including a base, a peripheral barrier and a rotatable cavity, said rotatable cavity comprising an inner surface of said base and an inner surface of said peripheral barrier, where said inner surface of said base and said inner surface of said peripheral barrier are configured to rotate around an axis of rotation and are configured to accommodate the storage of said insertion tube, and where at least one of said inner surface of said base and said inner surface of said peripheral barrier is configured to make physical contact with said insertion tube so that transfer of said insertion tube to or from said rotatable cavity causes said rotatable cavity to rotate without said insertion tube being fixably attached to said storage carousel;

where said insertion tube has both a proximal end and a distal end;

where said rotatable cavity is of a conical shape and where said rotatable cavity of said conical shape has a larger diameter located more proximate to said base and a smaller diameter located less proximate to said base; and where said storage carousel is located within a case, said case storing components at least one of a borescope and endoscope device.

5. An apparatus for storing an insertion tube of a borescope and an endoscope, said apparatus comprising:

a storage carousel including a base, a peripheral barrier and a rotatable cavity, said rotatable cavity comprising an inner surface of said base and an inner surface of said peripheral barrier, where said inner surface of said base and said inner surface of said peripheral barrier are configured to rotate around an axis of rotation and are configured to accommodate the storage of said insertion tube, and where at least one of said inner surface of said base and said inner surface of said peripheral barrier is configured to make physical contact with said insertion tube so that transfer of said insertion tube to or from said rotatable cavity causes said rotatable cavity to rotate without said insertion tube being fixably attached to said storage carousel;

where said insertion tube has both a proximal end and a distal end;

where said rotatable cavity is of a conical shape and where said rotatable cavity of said conical shape has a larger diameter located more proximate to said base and a smaller diameter located less proximate to said base; and where said storage carousel is attached to an outer surface of a case, said case storing components at least one of a borescope and endoscope device.

6. An apparatus for storing an insertion tube of a borescope and an endoscope, said apparatus comprising:

a storage carousel including a base, a peripheral barrier and a rotatable cavity, said rotatable cavity comprising an inner surface of said base and an inner surface of said peripheral barrier, where said inner surface of said base and said inner surface of said peripheral barrier are configured to rotate around an axis of rotation and are configured to accommodate the storage of said insertion tube, and where at least one of said inner surface of said base and said inner surface of said peripheral barrier is configured to make physical contact with said insertion tube so that transfer of said insertion tube to or from said rotatable cavity causes said rotatable cavity to rotate without said insertion tube being fixably attached to said storage carousel;

where said insertion tube has both a proximal end and a distal end;

where said rotatable cavity is of a conical shape and where said rotatable cavity of said conical shape has a larger diameter located more proximate to said base and a smaller diameter located less proximate to said base; and where said storage carousel is located separate from a case, said case storing components at least one of a borescope and endoscope device.

7. An apparatus for storing an elongated flexible object, said apparatus including:

a storage carousel having a base, a peripheral barrier, and an axis of rotation, said base substantially defining at least one inner surface that intersects said axis of rotation, said peripheral barrier having a conical shaped inner surface that surrounds said axis of rotation; and a rotatable cavity comprising said inner surface of said base and said inner surface of said peripheral barrier, said storage carousel configured to rotate around said axis of rotation and said rotatable cavity configured to accommodate the storage of an elongated flexible object disposed along at least one of said inner surface of said peripheral barrier and said inner surface of said base, said elongated flexible object having both a proximal end and a distal end;

where at least one of said inner surface of said base and said inner surface of said peripheral barrier is configured to make physical contact with and generate a frictional force with said elongated flexible object to cause said rotatable cavity to rotate;

where said storage carousel includes a conical shaped peripheral barrier, said conical shaped peripheral barrier including an inner surface having a larger inner diameter located proximate to said base and a smaller inner diameter located farther away from said base; and where said elongated flexible object is an insertion tube for at least one of a borescope and an endoscope device.

* * * * *

UNITED STATES PATENT AND TRADEMARK OFFICE
CERTIFICATE OF CORRECTION

| | | |
|---|---|---|
| PATENT NO. | : 7,819,798 B2 | Page 1 of 1 |
| APPLICATION NO. | : 11/474142 | |
| DATED | : October 26, 2010 | |
| INVENTOR(S) | : Krauter et al. | |

It is certified that error appears in the above-identified patent and that said Letters Patent is hereby corrected as shown below:

In Column 18, Line 2, delete "10a" and insert -- 110a --, therefor.

In Column 19, Line 18, delete "transparent-peripheral" and insert -- transparent peripheral --, therefor.

In Column 19, Line 40, delete "10d" and insert -- 110d --, therefor.

In Column 19, Line 44, delete "10d." and insert -- 110d. --, therefor.

Signed and Sealed this
Tenth Day of May, 2011

David J. Kappos
*Director of the United States Patent and Trademark Office*